US012594073B2

(12) United States Patent
Nakamura et al.

(10) Patent No.: US 12,594,073 B2
(45) Date of Patent: Apr. 7, 2026

(54) MEDICAL STAPLER AND SUTURING METHOD

(71) Applicant: OLYMPUS CORPORATION, Tokyo (JP)

(72) Inventors: Takashi Nakamura, Saitama (JP); Chisato Karasawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 92 days.

(21) Appl. No.: 18/596,894

(22) Filed: Mar. 6, 2024

(65) Prior Publication Data

US 2024/0206872 A1    Jun. 27, 2024

Related U.S. Application Data

(63) Continuation of application No. PCT/JP2021/033269, filed on Sep. 10, 2021.

(51) Int. Cl.
*A61B 17/068* (2006.01)
*A61B 17/00* (2006.01)

(52) U.S. Cl.
CPC .... *A61B 17/0684* (2013.01); *A61B 17/00234* (2013.01); *A61B 2017/00296* (2013.01); *A61B 2017/00367* (2013.01); *A61B 2017/00738* (2013.01)

(58) Field of Classification Search
CPC .......... A61B 17/00234; A61B 17/0684; A61B 17/072; A61B 17/07207; A61B 17/29; A61B 2017/00296; A61B 2017/00367; A61B 2017/00738; A61B 2017/00818;
(Continued)

(56) References Cited

U.S. PATENT DOCUMENTS

2004/0059346 A1* 3/2004 Adams ............. A61B 17/07207
606/115
2015/0359534 A1 12/2015 Gibbons, Jr.
2018/0042603 A1 2/2018 Mitelberg et al.
(Continued)

FOREIGN PATENT DOCUMENTS

EP        2436319 A2   4/2012
JP     2000166936 A   6/2000
(Continued)

OTHER PUBLICATIONS

"International Application Serial No. PCT/JP2021/033269, International Search Report dated Dec. 7, 2021", w/ English Translation, (Dec. 7, 2021), 4 pgs.

*Primary Examiner* — Robert A Lynch
(74) *Attorney, Agent, or Firm* — Schwegman Lundberg & Woessner, P.A.

(57) ABSTRACT

A medical stapler includes a stapling head including a staple ejection portion, an anvil openably and closably coupled to the stapling head by a rotation shaft, a staple receiving portion provided in the anvil and provided at a position facing the staple ejection portion when the stapling head and the anvil are in a closed state, a lever rotatably provided on the stapling head, and a lever operation wire connected to the lever and provided to extend in a direction of a proximal end of the stapling head, in which the lever is capable of raising upward with respect to the stapling head in accordance with advance and retraction of the lever operation wire.

14 Claims, 30 Drawing Sheets

(58) Field of Classification Search
        CPC ........... A61B 2017/07257; A61B 2017/07271;
                                           A61B 2017/07278
        See application file for complete search history.

(56)                          References Cited

U.S. PATENT DOCUMENTS

2020/0100784  A1 *    4/2020   Farascioni  ........... A61B 17/068
2021/0022733  A1       1/2021   Smith et al.

FOREIGN PATENT DOCUMENTS

JP            2001507615  A       6/2001
JP            2004503325  A       2/2004
JP            2012075868  A       4/2012
WO          WO-9922649  A2       5/1999
WO          WO-0205721  A2       1/2002

* cited by examiner

MEDICAL STAPLER AND SUTURING METHOD

This application is a continuation application of PCT International Application No. PCT/JP2021/033269, filed on Sep. 10, 2021. The content of the above-identified PCT International Applications is incorporated herein by reference.

TECHNICAL FIELD

The present disclosure relates to a medical stapler and a suturing method.

BACKGROUND ART

In recent years, a medical stapler such as a stapler has been used in a surgery for suturing the digestive tract or the like. When an appropriate medical stapler is used, the surgery for suturing the digestive tract or the like can be made easier and a surgical time can be significantly reduced.

As a conventional medical stapler, for example, there is one including an endoscope and a stapling mechanism disposed around the endoscope disclosed in United States Patent Application, Publication No. 2018/0042603 (hereinafter, referred to as Patent Document). In the configuration of the Patent Document, a suturing treatment on a treatment target can be performed by the stapling mechanism while observing the treatment target using the endoscope.

However, when the medical stapler described in the Patent Document is used to suture a tissue (treatment target) in which a lesion has been found using the stapling mechanism, it has been difficult to ascertain a suture position and whether or not suturing is possible with the treatment target fully included.

In view showing the above circumstances, an objective of the present disclosure is to provide a medical stapler and a suturing method capable of causing a suture position to be easily ascertained and improving a treatment effect.

SUMMARY

In order to solve the above problems, the present disclosure proposes the following aspects.

A medical stapler according to a first aspect of the present disclosure includes a stapling head including a staple ejection portion, an anvil openably and closably coupled to the stapling head by a rotation shaft, a staple receiving portion provided in the anvil and provided at a position facing the staple ejection portion when the stapling head and the anvil are in a closed state, a lever rotatably provided on the stapling head, and a lever operation wire connected to the lever and provided to extend in a direction of a proximal end of the stapling head. The lever is capable of raising upward with respect to the stapling head in accordance with advance and retraction of the lever operation wire.

A medical stapler according to a second aspect of the present disclosure includes a stapling head including a staple ejection portion, an anvil openably and closably coupled to the stapling head by a rotation shaft, a staple receiving portion provided in the anvil and provided at a position facing the staple ejection portion when the stapling head and the anvil are in a closed state, and a temporarily immobilizing portion provided in the stapling head and being able to temporarily immobilize a treatment target with respect to the stapling head.

A suturing method according to a third aspect of the present disclosure includes an insertion step of inserting a medical stapler and an endoscope into the body, an advancing step of causing a treatment tool to protrude from the endoscope and advancing the treatment tool with respect to the medical stapler, a first open-close step of bringing an anvil into an open state with respect to a stapling head at a portion close to a treatment target, a grasping step of grasping a tissue containing the treatment target inside the body with the treatment tool, a retracting step of retracting the treatment tool relative to the medical stapler to draw in the treatment target to a proximal-end side of the medical stapler with respect to a staple ejection position, a second open-close step of bringing the anvil into a closed state with respect to the stapling head to fix the tissue, a lever raising step of raising a lever upward with respect to the stapling head, an observation step of projecting the treatment target within a field of view showing the endoscope, and a suturing step of ejecting a staple from the stapling head of the medical stapler to suture a circumference of the treatment target.

A suturing method according to a fourth aspect of the present disclosure includes an insertion step of inserting a medical stapler and an endoscope into the body, an advancing step of causing a treatment tool to protrude from the endoscope and advancing the treatment tool with respect to the medical stapler, a first open-close step of bringing an anvil into an open state with respect to a stapling head at a portion close to a treatment target, a lever raising step of raising a lever upward with respect to the stapling head, a grasping step of grasping a tissue containing the treatment target inside the body with the treatment tool, a retracting step of retracting the treatment tool relative to the medical stapler to draw in the treatment target to a proximal-end side of the medical stapler with respect to a staple ejection position, a second open-close step of bringing the anvil into a closed state with respect to the stapling head, a pressing step of pressing the treatment target drawn in to the endoscope side from above by lowering the lever, an observation step of projecting the treatment target within a field of view showing the endoscope, and a suturing step of ejecting a staple from the stapling head of the medical stapler to suture a circumference of the treatment target.

Advantageous Effects of Invention

The medical stapler of the present disclosure can cause a suture position to be easily ascertained for a tissue inside the body and improve a treatment effect.

BRIEF DESCRIPTION OF DRAWINGS

FIG. 8 is a side view showing the medical stapler with the grasping portion in a closed state.

FIG. 14 is a cross-sectional view showing the grasping portion in which an ejection operation wire is pulled.

DESCRIPTION OF EMBODIMENTS

First Embodiment

A first embodiment of the present disclosure will be described with reference to FIGS. 1 to 21.

Figure 1:
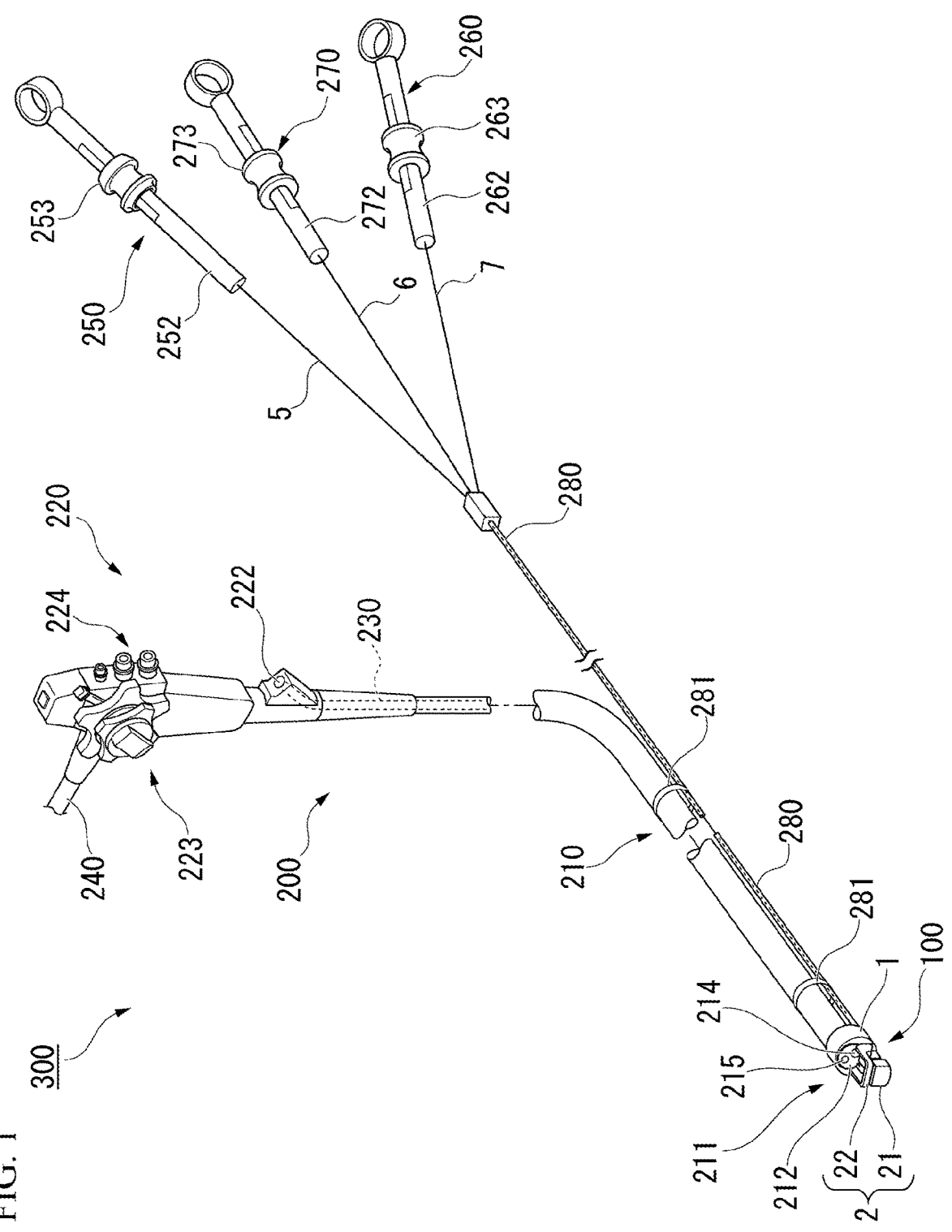
FIG. 1 is a view showing an overall configuration of a medical system including a medical stapler according to an embodiment.

FIG. 1 is a view showing an overall configuration of a medical system 300 including a medical stapler 100 according to the present embodiment.

[Medical System 300]

The medical system 300 is used for a surgery or the like in which the digestive tract or the like is sutured. The medical system 300 includes a medical stapler 100, an endoscope 200, an open-close operation unit 250, a lever operation unit 260, an ejection operation unit 270, and a wire sheath 280. The open-close operation unit 250 is an operation unit that operates the medical stapler 100 using an open-close operation wire 5. The lever operation unit 260 is an operation unit that operates the medical stapler 100 using a lever operation wire 7. The ejection operation unit 270 is an operation unit that operates the medical stapler 100 using an ejection operation wire 6.

[Endoscope 200]

The endoscope 200 is a known flexible endoscope, and includes a long insertion portion 210 that is inserted into the body from a distal end thereof, an operation unit 220 provided at a proximal-end portion of the insertion portion 210, and a universal cord 240.

A treatment tool channel 230 through which an endoscopic treatment tool is inserted is formed in the insertion portion 210. A forceps port 214, which is a distal end opening of the treatment tool channel 230, is provided at a distal end 212 of the insertion portion 210. The treatment tool channel 230 extends from the distal end 212 of the insertion portion 210 to the operation unit 220.

A distal-end portion 211 of the insertion portion 210 includes an imaging unit (not shown in the drawings) including a CCD or the like. An objective lens 215 of the imaging unit is exposed at the distal end 212 of the insertion portion 210.

A knob 223 that operates the insertion portion 210 and a switch 224 that operates the imaging unit or the like are provided on a proximal-end side of the operation unit 220. An operator can bend the insertion portion 210 in a desired direction by operating the knob 223.

A forceps insertion port 222 communicating with the treatment tool channel 230 is provided on a distal-end side of the operation unit 220. The operator can insert the endoscopic treatment tool into the treatment tool channel 230 through the forceps insertion port 222.

The universal cord 240 connects the operation unit 220 and an external peripheral device. The universal cord 240 outputs, for example, an image captured by the imaging unit to an external device. The image captured by the imaging unit is displayed on a display device such as a liquid crystal display via an image processing device.

[Open-Close Operation Unit 250]

The open-close operation unit 250 is an operation unit that opens and closes the medical stapler 100 by operating the open-close operation wire 5. As shown in FIG. 1, the open-close operation unit 250 includes an open-close operation unit main body 252 and an open-close operation slider 253. A proximal end of the open-close operation wire 5 is coupled to the open-close operation slider 253. The operator can advance and retract the open-close operation wire 5 by advancing and retracting the open-close operation slider 253 in a longitudinal axis direction with respect to the open-close operation unit main body 252.

[Lever Operation Unit 260]

The lever operation unit 260 is an operation unit that operates rotation of a lever 50 (FIG. 2) of the medical stapler 100 by operating the lever operation wire 7. As shown in FIG. 1, the lever operation unit 260 includes a lever operation unit main body 262 and a lever operation slider 263. A proximal end of the lever operation wire 7 is coupled to the lever operation slider 263. The operator can advance and retract the lever operation wire 7 by advancing and retracting the lever operation slider 263 in a longitudinal axis direction with respect to the lever operation unit main body 262.

[Ejection Operation Unit 270]

The ejection operation unit 270 is an operation unit that ejects a staple S (FIG. 10) from the medical stapler 100 by operating the ejection operation wire 6. As shown in FIG. 1, the ejection operation unit 270 includes an ejection operation unit main body 272 and an ejection operation slider 273. A proximal end of the ejection operation wire 6 is coupled to the ejection operation slider 273. The operator can move the ejection operation wire 6 by advancing and retracting the ejection operation slider 273 in a longitudinal axis direction with respect to the ejection operation unit main body 272.

[Wire Sheath 280]

Figure 12:
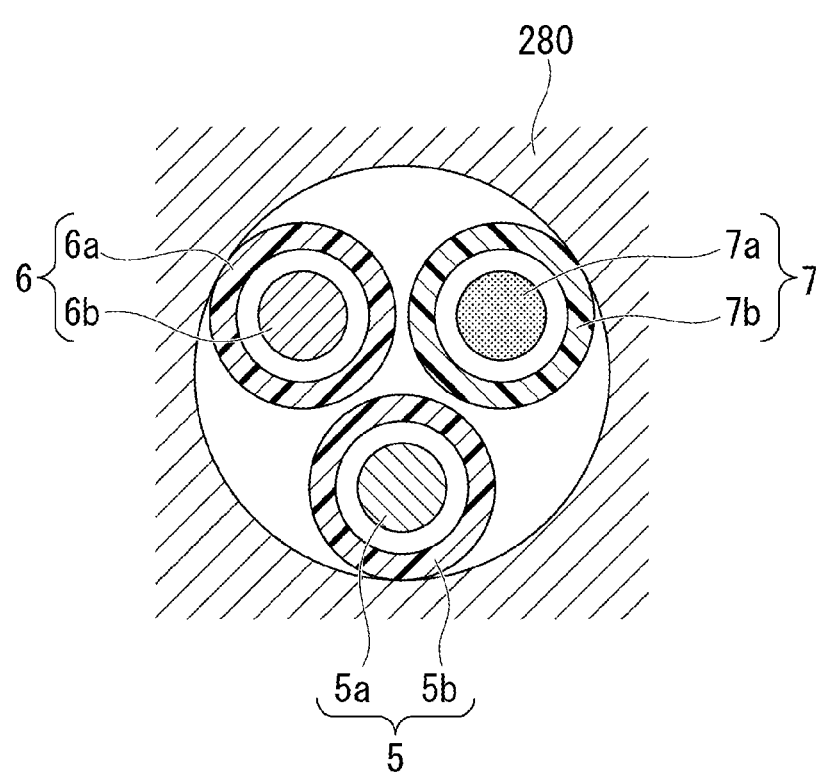
FIG. 12 is a cross-sectional view showing a wire sheath shown in FIG. 11.

The wire sheath 280 is a sheath through which the open-close operation wire 5, the ejection operation wire 6, and the lever operation wire 7 are inserted. As shown in FIGS. 1 and 12, a distal-end side of the wire sheath 280 is coupled to the insertion portion 210 of the endoscope 200 by a plurality of bands 281.

[Medical Stapler 100]

Figure 2:
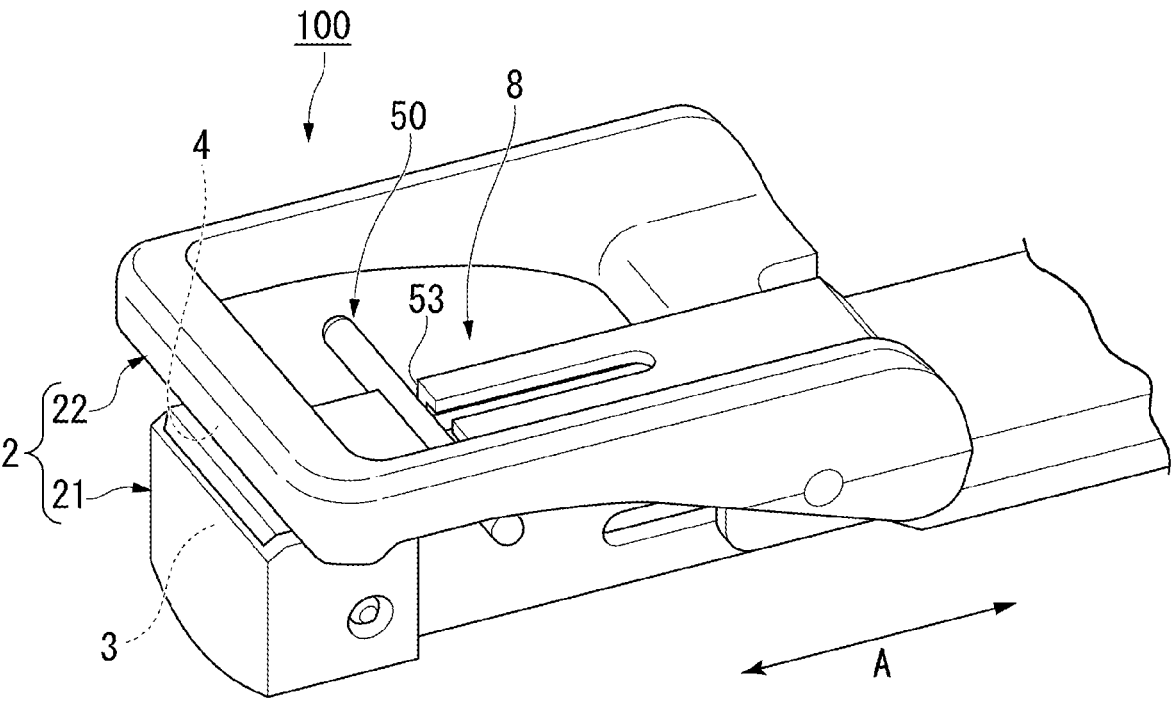
FIG. 2 is a perspective view showing the medical stapler.

FIG. 2 is a perspective view showing the medical stapler 100.

The medical stapler 100 includes a cap 1, a grasping portion 2, a lever portion 8, a staple ejection portion 3, a staple receiving portion 4, the open-close operation wire 5, and the ejection operation wire (power transmission member) 6. The medical stapler 100 is attachable to and detachable from the distal-end portion 211 of the insertion portion 210 shown in FIG. 1.

Figure 3:
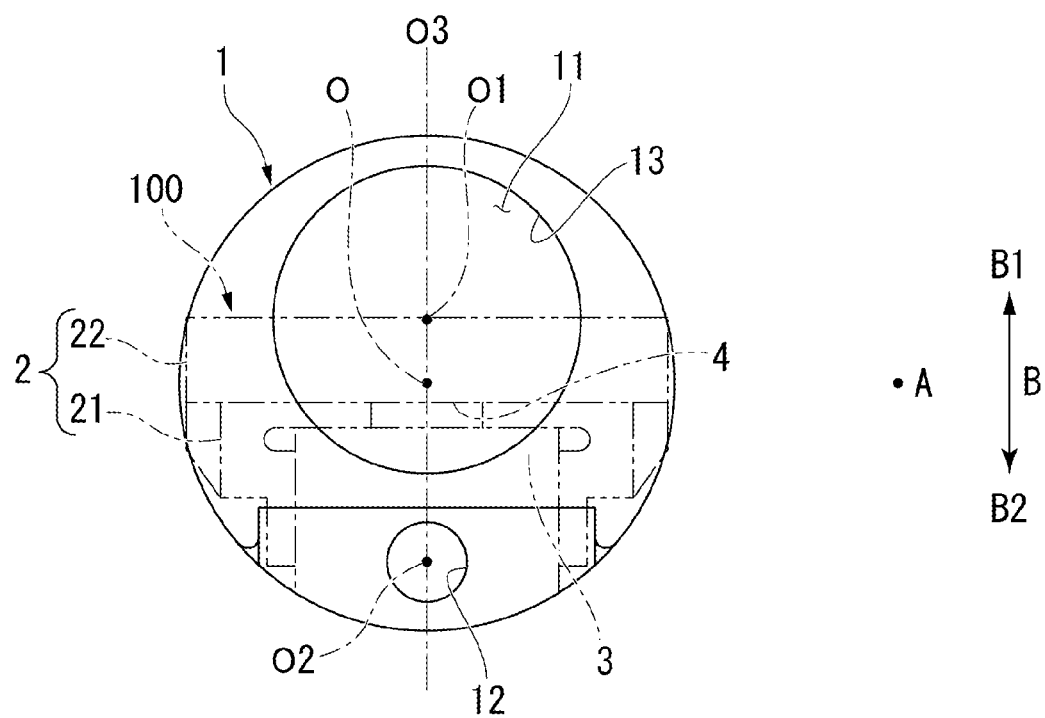
FIG. 3 is a front view showing a cap.

FIG. 3 is a front view showing the cap 1. In FIG. 3, the grasping portion 2 is displayed in a transparent manner.

The cap (attachment member) 1 is a member that is attachable to the distal-end portion 211 of the endoscope 200. The cap 1 is formed in a substantially columnar shape and has a first through hole 11 penetrating in an axial direction A (FIG. 2) and a second through hole 12 penetrating in the axial direction A.

The first through hole 11 is a hole into which the distal-end portion 211 of the insertion portion 210 shown in FIG. 1 is inserted. A shape of the first through hole 11 is formed to follow an outer shape of the distal-end portion 211 of the insertion portion 210. Therefore, when the distal-end portion 211 of the endoscope 200 is inserted into the first through hole 11, the cap 1 can be attached to the distal-end portion 211 of the endoscope 200.

A central axis O1 of the first through hole 11 in the axial direction A is eccentric with respect to a central axis O of the cap 1 in the axial direction A. A direction in which the central axis O1 is eccentric with respect to the central axis O is defined as an "upward side B1".

The second through hole 12 is a hole into which the wire sheath 280, through which the open-close operation wire 5, the ejection operation wire 6, and the lever operation wire 7 shown in FIG. 1 are inserted, is inserted. An inner diameter of the second through hole 12 is substantially coincident with an outer diameter of the wire sheath 280.

A distal-end portion of the wire sheath 280 is inserted through the second through hole 12 to be fixed. The open-close operation wire 5, the ejection operation wire 6, and the lever operation wire 7 which are inserted through the wire sheath 280 pass through the second through hole 12 and extend to a distal-end side thereof.

The central axis O2 of the second through hole 12 in the axial direction A is eccentric with respect to the central axis O of the cap 1 in the axial direction A as shown in FIG. 3. A direction in which the central axis O2 is eccentric with respect to the central axis O is opposite to the direction (the upward side B1) in which the central axis O1 is eccentric with respect to the central axis O. A direction in which the central axis O2 is eccentric with respect to the central axis O is defined as a "downward side B2". In the present embodiment, the upward side B1 and the downward side B2 are directions extending in a vertical direction B.

Figure 4:
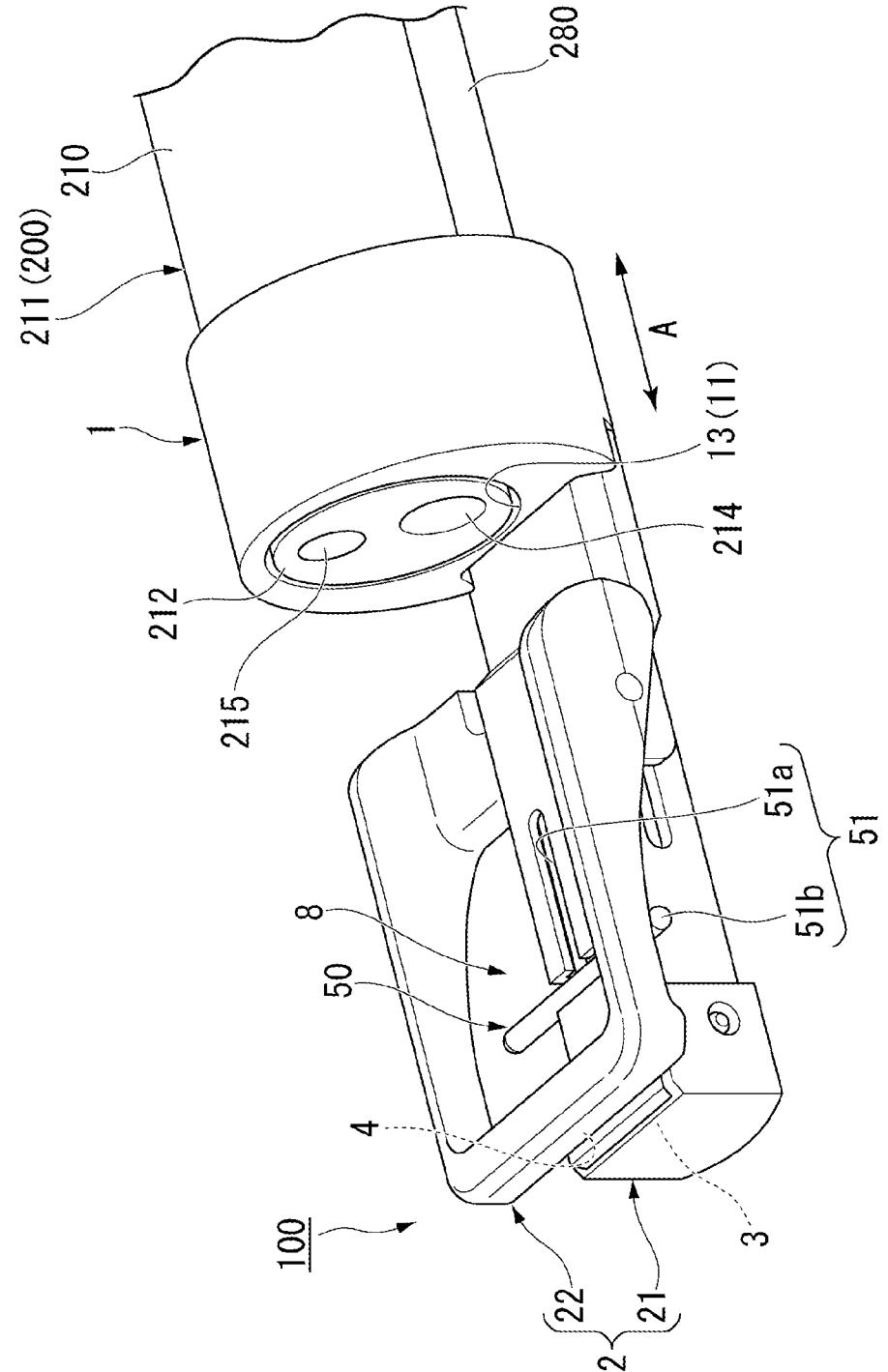
FIG. 4 is a perspective view showing the medical stapler with a grasping portion in a closed state.
Figure 5:
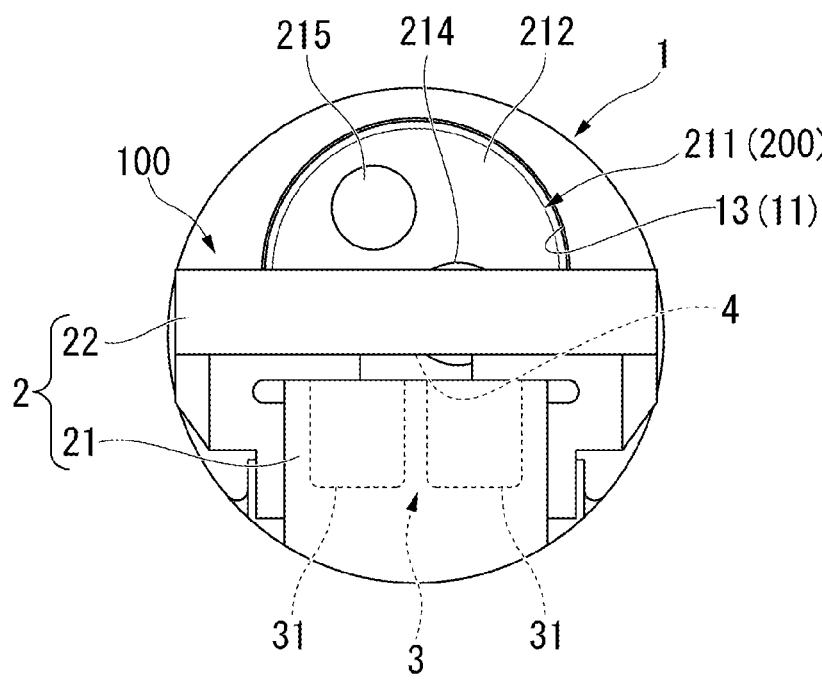
FIG. 5 is a front view showing the medical stapler with the grasping portion in a closed state.

FIG. 4 is a perspective view showing the medical stapler 100 with the grasping portion 2 in a closed state. FIG. 5 is a front view showing the medical stapler 100 with the grasping portion 2 in a closed state.

When the cap 1 is attached to the distal-end portion 211 of the endoscope 200, as shown in FIGS. 4 and 5, the objective lens 215 and the forceps port 214 are exposed from an opening 13 on a distal-end side of the first through hole 11 of the cap 1. The operator can observe a treatment target through the objective lens 215 even when the medical stapler 100 is attached to the distal-end portion 211 of the endoscope 200.

Figure 6:
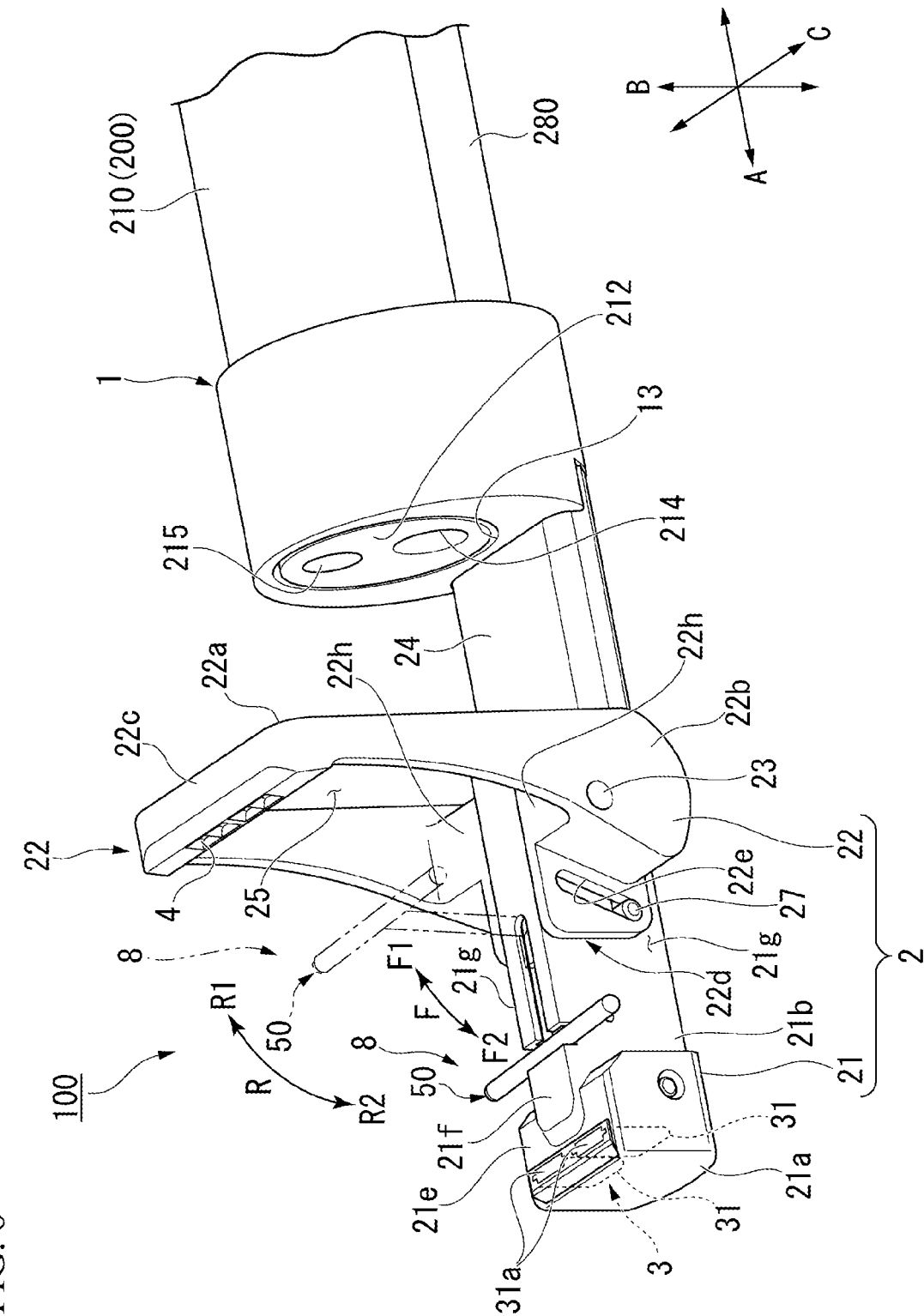
FIG. 6 is a perspective view showing the medical stapler with the grasping portion in an open state.
Figure 7:
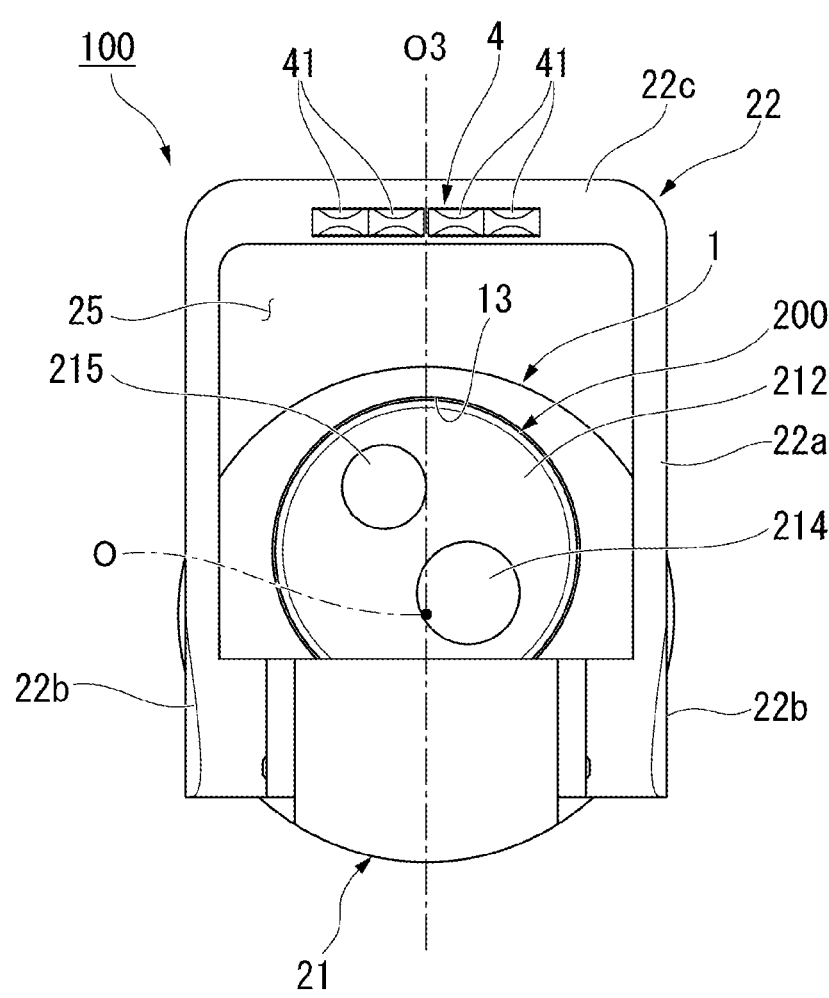
FIG. 7 is a front view showing the medical stapler with the grasping portion in an open state.
Figure 8:
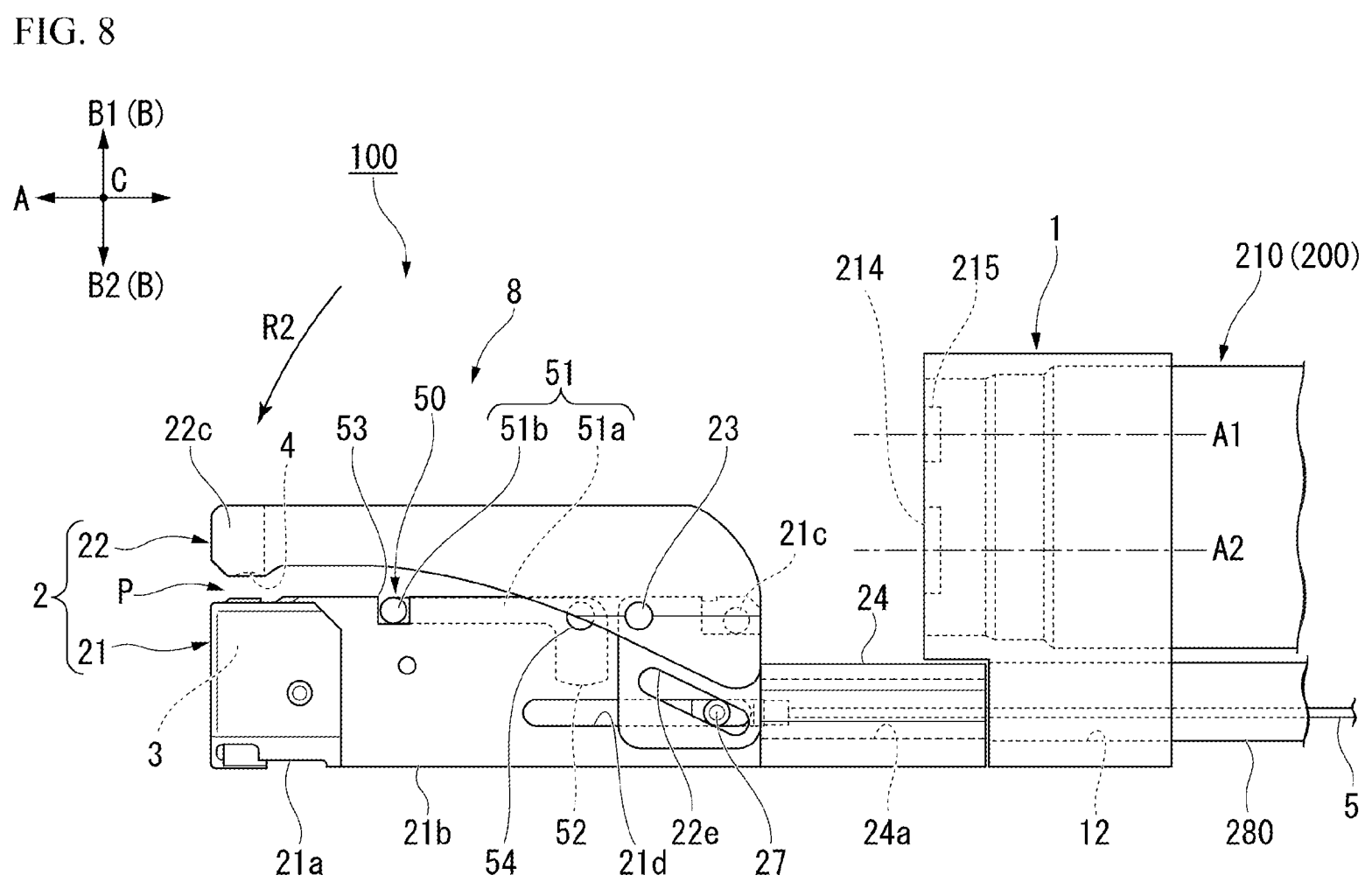
Figure 9:
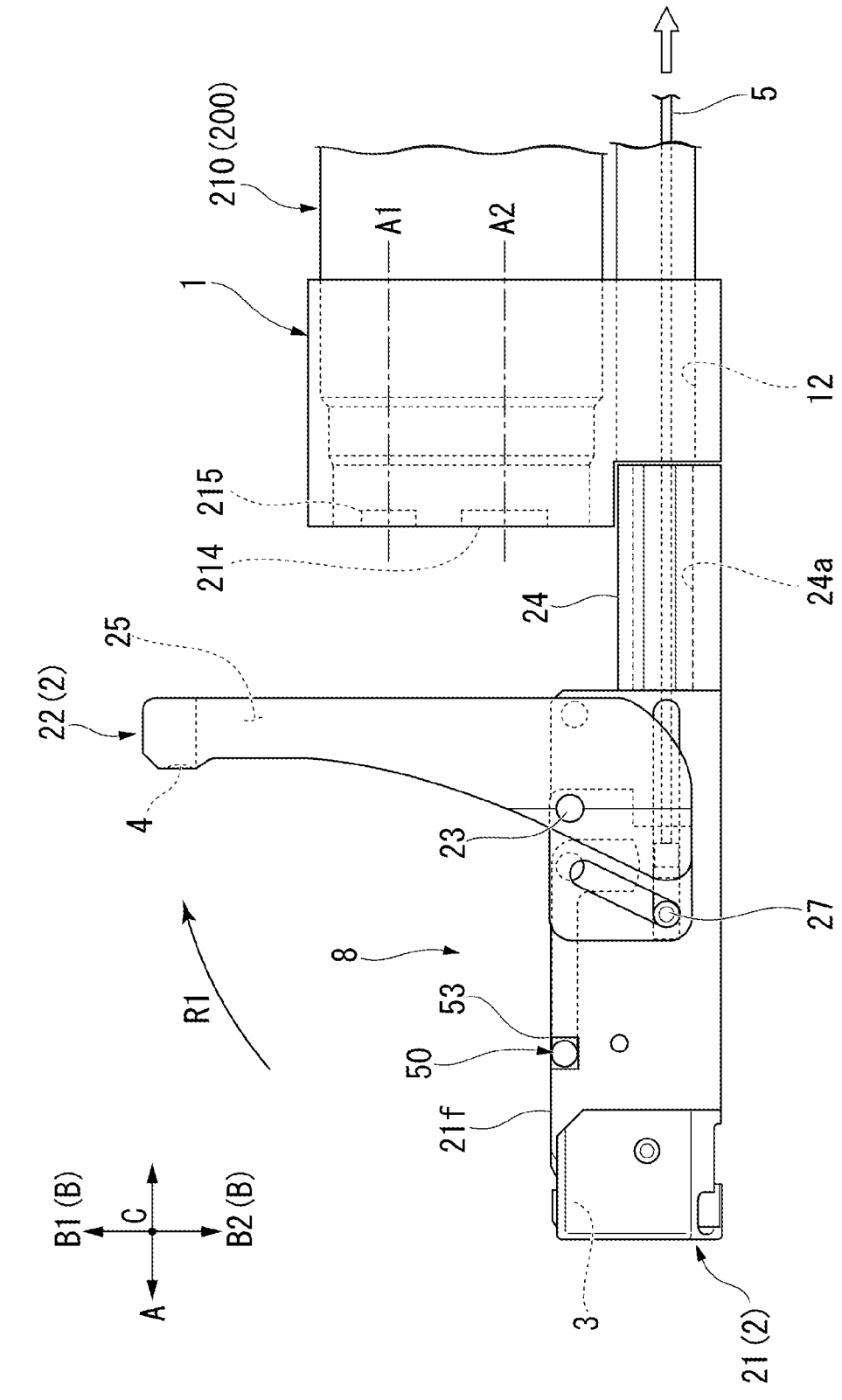
FIG. 9 is a side view showing the medical stapler with the grasping portion in an open state.

FIG. 6 is a perspective view showing the medical stapler 100 with the grasping portion 2 in an open state. FIG. 7 is a front view showing the medical stapler 100 with the grasping portion 2 in an open state. Further, FIG. 8 is a side view showing the medical stapler 100 with the grasping portion 2 in a closed state. FIG. 9 is a side view showing the medical stapler 100 with the grasping portion 2 in an open state.

As shown in FIG. 6, the grasping portion 2 includes a stapling head (first grasping member) 21, an anvil (second grasping member) 22, an open-close rotation shaft (rotation shaft) 23, and a movable pin 27.

The stapling head 21 and the anvil 22 are coupled to be openable and closable by the open-close rotation shaft 23. The open-close rotation shaft 23 is provided on the distal-end side with respect to the cap 1. An axial direction C of the open-close rotation shaft 23 is perpendicular to the axial direction A and the vertical direction B of the cap 1. As shown in FIG. 7, the grasping portion 2 is symmetrically formed with respect to the central axis O3 in the vertical direction B.

The stapling head 21 is non-rotatably fixed to the distal-end side of the cap 1. The stapling head 21 is fixed to the cap 1 at a position on the downward side B2 with respect to the central axis O of the cap 1. As shown in FIG. 3, the stapling head 21 is disposed at a position overlapping the second through hole 12 of the cap 1 in a front view. On the other hand, as shown in FIG. 7, the stapling head 21 is disposed at a position not overlapping the objective lens 215 and the forceps port 214 of the endoscope 200 in a front view.

The stapling head 21 includes the staple S (FIG. 10) and the staple ejection portion 3 (FIG. 6). As shown in FIG. 6, the stapling head 21 includes a first distal-end portion 21*a* and a first main body portion 21*b*, and is formed in a substantially T shape when viewed from above. The first distal-end portion 21*a* is disposed on the distal-end side with respect to the first main body portion 21*b*.

The first distal-end portion 21*a* is formed in a substantially rectangular parallelepiped shape. The first distal-end portion 21*a* is formed in a rectangular shape extending in the axial direction C of the open-close rotation shaft 23 in a plan view. The staple ejection portion 3 is provided at the first distal-end portion 21*a*. An opening 31*a* of the staple ejection portion 3 is provided on a surface (upper surface 21*e*) of the first distal-end portion 21*a* on the upward side B1.

The first main body portion 21*b* is an elongated member extending in the axial direction A. A distal end of the first main body portion 21*b* is fixed to the first distal-end portion 21*a*. A proximal end of the first main body portion 21*b* is fixed to the cap 1 via an extended portion 24.

In the present embodiment, the extended portion 24 for securing a distance from the endoscope 200 is provided on a proximal-end side of the grasping portion 2, but the present embodiment is not limited to this configuration. Presence or absence, a length, or the like of the extended portion 24 can be appropriately selected and changed according to a configuration of the grasping portion 2 and other factors such as a size of grasping forceps (treatment tool) G.

A communication hole 24*a* (FIG. 8) communicating with the second through hole 12 formed in the cap 1 is formed in the extended portion 24, and through which the open-close operation wire 5, the ejection operation wire 6 (FIG. 1), and the lever operation wire 7 (FIG. 1) are inserted.

Further, in the present embodiment, the extended portion 24 is provided in the grasping portion 2, but the extended portion 24 may be provided in the cap 1.

The first main body portion 21*b* includes a contact pin 21*c* (FIG. 8). The contact pin 21*c* is provided at the proximal end of the first main body portion 21*b* and comes into contact with the anvil 22 in a closed state to restrict a movable range of the anvil 22.

As shown in FIG. 8, a first engagement groove 21*d* is a groove penetrating in the axial direction C of the open-close rotation shaft 23 in the first main body portion 21*b*. The first engagement groove 21*d* extends in the axial direction A.

The medical stapler 100 includes the lever portion 8 on the stapling head 21 side. The lever portion 8 includes a lever 50 and a lever rotation shaft 54.

The lever portion 8 is provided at the first main body portion 21*b* of the stapling head 21. The lever portion 8 is such that the lever 50 is rotatably provided with respect to the stapling head 21, and can be operated independently of the anvil 22.

It is possible to rotate the lever 50 around an axis of the lever rotation shaft 54 to raise it upward by an operation of advancing and retracting the lever operation wire 7 shown in FIG. 1. The lever 50 can be accommodated in a lever accommodating groove 53 formed in the first main body portion 21*b* of the stapling head 21. As shown in FIG. 6, the lever accommodating groove 53 is a T-shaped groove in a plan view that opens on an upper surface 21*f* and both side surfaces 21*g* of the first main body portion 21*b*.

The lever 50 includes a main body portion 51 formed in a substantially T shape as shown in FIG. 6, and a support portion 52 supporting the main body portion 51 to be rotatable as shown in FIG. 8. The main body portion 51 is a portion that can be exposed from the lever accommodating groove 53, and is formed in a T shape. As shown in FIGS. 4 and 8, the main body portion 51 includes a first portion 51*a* that can extend in the axial direction A, and a second portion 51*b* that is positioned at a distal end of the first portion 51*a* and extends perpendicularly in the axial direction C. The second portion 51*b* is longer than the width dimension of the stapling head 21, and both ends thereof protrude from both sides of the stapling head 21 in a width direction when it is in an accommodated state. The main body portion 51 is formed in a size that allows it to pass through a visual space (first visual space) 25 to be described later.

As shown in FIG. 8, the support portion 52 is positioned at a proximal end of the main body portion 51 (first portion 51*a*) and extends in a direction orthogonal to the first portion 51*a* and the second portion 51*b*.

As shown in FIG. 8, the lever 50 is rotatably attached to the stapling head 21 by the lever rotation shaft 54 provided at a connection position between the main body portion 51 and the support portion 52. The lever rotation shaft 54 is connected to a proximal end of the lever 50 to rotate the lever 50. The lever rotation shaft 54 is positioned in front of the open-close rotation shaft 23 and is parallel to the open-close rotation shaft 23 extending in the width direction of the stapling head 21.

The anvil 22 is attached to the stapling head 21 to be rotatable by the open-close rotation shaft 23. As shown in FIGS. 6 and 7, the anvil 22 includes a U-shaped member 22*a* formed in a substantially U shape, and a pair of second main body portions 22*b* that support the U-shaped member 22*a* to be rotatable.

The U-shaped member 22*a* is formed in a substantially U-shape, and both end parts thereof are coupled to the second main body portions 22*b*. In a closed state, a central portion of the U-shaped member 22*a* is disposed on a distal-end side of the stapling head 21. The central portion includes a second distal-end portion 22*c*. The second distal-end portion 22*c* is formed in a substantially rectangular parallelepiped shape. The second distal-end portion 22*c* extends in the axial direction C of the open-close rotation shaft 23. The staple receiving portion 4 is provided at the second distal-end portion 22*c*.

The second main body portions 22*b* are each rotatably attached to the first main body portion 21*b* of the stapling head 21 by the open-close rotation shaft 23. A second engagement groove 22*e* is formed in each of the second main body portion 22*b*.

The second engagement groove 22*e* is a groove that penetrates in the axial direction C. As shown in FIG. 7, the second engagement groove 22*e* is symmetrical with respect to the central axis O3 of the anvil 22. As shown in FIG. 8, the second engagement groove 22*e* is inclined toward the downward side B2 as it goes from a distal-end side to a proximal-end side in the axial direction A in a side view in a closed state.

As shown in FIGS. 6 and 7, the anvil 22 has the visual space 25 that passes through in an open-close direction R between the staple receiving portion 4 on the distal-end side and the open-close rotation shaft 23 on the proximal-end side. In the present embodiment, the visual space 25 is a space surrounded by sides of the U-shaped member 22*a* formed in a substantially U shape.

As shown in FIG. 8, the movable pin 27 is engaged with the first engagement groove 21*d* and the second engagement groove 22*e*, and advances and retracts in the axial direction A along the first engagement groove 21*d*. A distal end of the open-close operation wire 5 is attached to the movable pin 27. The movable pin 27 advances and retracts in the axial direction A due to an operation of the open-close operation wire 5, and in conjunction with this, the anvil 22 opens and closes as shown in FIGS. 8 and 9.

When the open-close operation wire 5 retracts toward the rear end side, as shown in FIG. 9, the movable pin 27 rotates the anvil 22 in an opening direction (R1) with the open-close rotation shaft 23 as a center to bring the grasping portion 2 into an open state. When the open-close operation wire 5 advances toward the distal-end side, as shown in FIG. 8, the movable pin 27 rotates the anvil 22 in a closing direction (R2) with the open-close rotation shaft 23 as a center to bring the grasping portion 2 into a closed state.

When the grasping portion 2 is in a closed state, the staple ejection portion 3 and the staple receiving portion 4 face each other in the vertical direction B as shown in FIG. 8. When the grasping portion 2 is in the closed state, a slight gap P is formed between the staple ejection portion 3 and the staple receiving portion 4. When the grasping portion 2 is in the closed state, an optical axis A1 of the objective lens 215 passes outside (the upward side B1 of) the stapling head 21 and the anvil 22. Also, when the grasping portion 2 is in the closed state, a central axis A2 of the forceps port 214 is at a position not overlapping the stapling head 21 but overlapping the anvil 22 in a front view.

As shown in FIG. 9, when the grasping portion 2 is in an open state, the staple receiving portion 4 is disposed on the proximal-end side (rearward side) with respect to the open-close rotation shaft 23 in the axial direction A. When the grasping portion 2 is in the open state, the staple receiving portion 4 is disposed on the proximal-end side (rearward side) with respect to the staple ejection portion 3 in the axial direction A. When the grasping portion 2 is in the open state, the optical axis A1 of the objective lens 215 passes through the visual space 25. Also, when the grasping portion 2 is in the open state, the central axis A2 of the forceps port 214 passes through the visual space 25.

Figure 10:
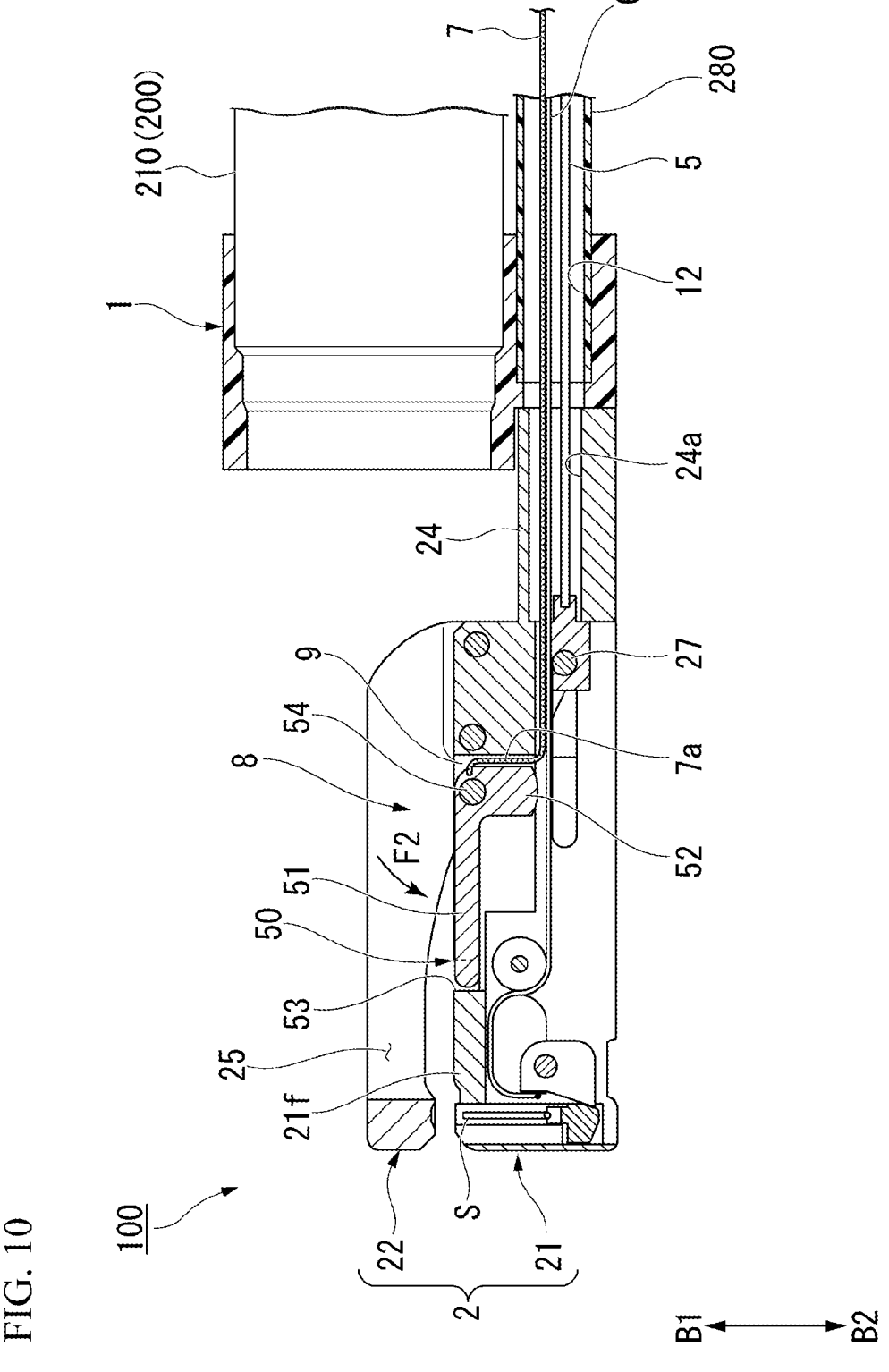
FIG. 10 is a cross-sectional view showing the medical stapler in which a lever is accommodated.
Figure 11:
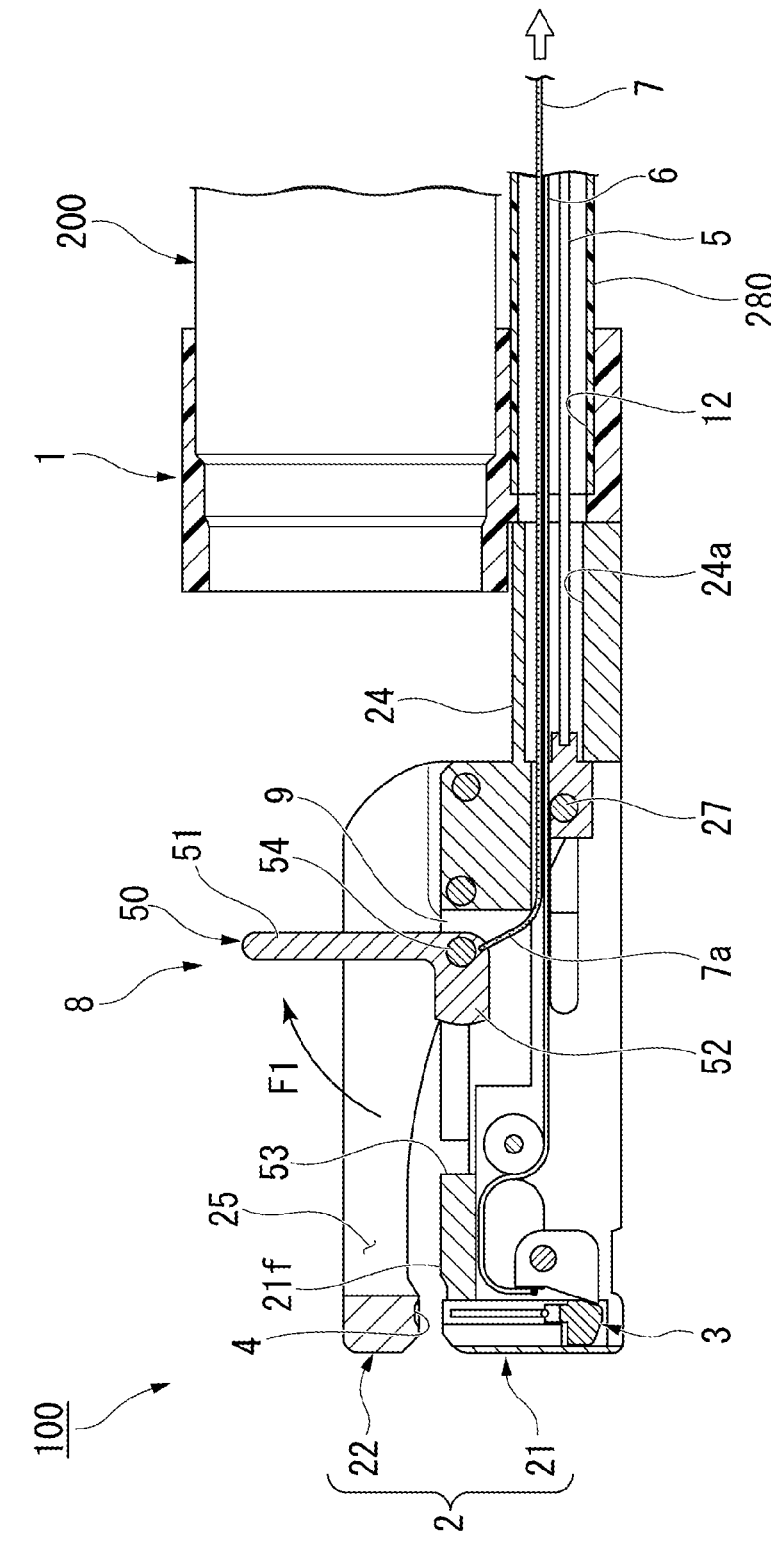
FIG. 11 is a cross-sectional view showing the medical stapler in which the lever is raised.

FIGS. 10 and 11 are cross-sectional views of the grasping portion 2 including the lever 50. FIG. 10 shows a state in which the lever 50 is accommodated, and FIG. 11 shows a state in which the lever 50 is raised.

As shown in FIGS. 10 and 11, a distal end 7a of the lever operation wire 7 is attached to the lever 50. When the lever 50 is rotated around the axis of the lever rotation shaft 54 by an operation of the lever operation wire 7, the lever 50 can be put in and taken out with respect to the lever accommodating groove 53.

As shown in FIG. 10, when the lever 50 is in a state of being accommodated, a distal-end side of the lever operation wire 7 is raised up toward the upward side B1 in the stapling head 21 and is connected to a boundary portion between the main body portion 51 and the support portion 52 at a portion close to the lever rotation shaft 54. The distal end 7a side of the lever operation wire 7 is connected to the lever 50 in a state in which it has entered a gap 9 formed between the lever rotation shaft 54 and the open-close rotation shaft 23 in the lever accommodating groove 53.

As shown in FIG. 6, a rotation direction F of the lever 50 is the same as the open-close direction R of the anvil 22. As shown in FIG. 11, when the lever operation wire 7 is pulled to a rear end side, the lever 50 is rotated in a protruding direction (F1) with the lever rotation shaft 54 as a center, and the main body portion 51 thereof is exposed from the inside of the lever accommodating groove 53 to assume a protruding orientation. A degree of protrusion (rising) of the main body portion 51 can be adjusted by an extent to which the lever operation wire 7 is pulled. When the main body portion 51 of the lever 50 rotates to the proximal-end side around the axis of the lever rotation shaft 54 and rises, the support portion 52 rotates to the distal-end side and moves to the distal-end side with respect to the lever rotation shaft 54. For example, the protruding orientation shown in FIG. 11 is an orientation at maximum pulling. When the lever has a maximum protruding orientation, the main body portion 51 extends in a vertical direction orthogonal to the lever rotation shaft 54.

As shown in FIG. 10, when the lever operation wire 7 advances toward the distal-end side, the lever 50 is rotated in an accommodating direction (F2) with the lever rotation shaft 54 as a center, and is entirely accommodated inside the lever accommodating groove 53 to assume an accommodated orientation. When the lever 50 assumes the accommodated orientation, the main body portion 51 extends in the axial direction A.

FIG. 12 is a cross-sectional view showing the wire sheath 280 shown in FIG. 11.

The open-close operation wire 5, the ejection operation wire 6, and the lever operation wire 7 are inserted through the inside of the wire sheath 280. These three wires 5, 6, and 7 are each constituted by wire main bodies 5a, 6a, and 7a, and resin sheaths 5b, 6b, and 7b.

Figure 13:
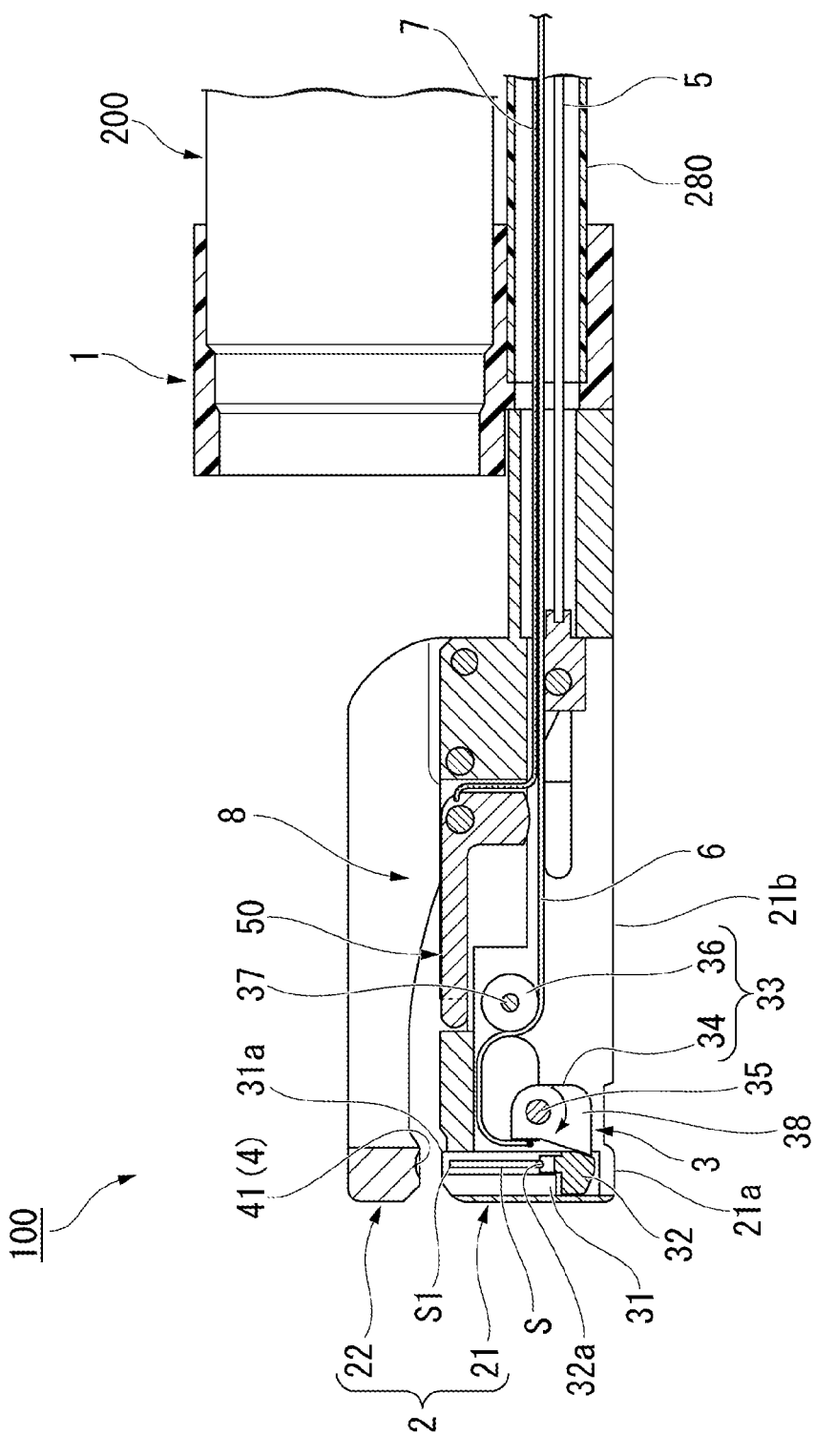
FIG. 13 is a cross-sectional view showing the grasping portion including a staple ejection portion.

FIG. 13 is a cross-sectional view showing the grasping portion 2 including the staple ejection portion 3. FIG. 13 shows a state before the ejection operation wire 6 is pulled.

The staple ejection portion 3 is provided at the first distal-end portion 21a of the stapling head 21, and can store and eject the staple S. The staple ejection portion 3 includes a staple storage portion 31, a linear movement member 32, and a rotation member 33.

The staple storage portion 31 is a space that stores the staple S provided at the first distal-end portion 21a of the stapling head 21. As shown in FIG. 6, the stapling head 21 includes two staple storage portions 31 formed to be aligned in the axial direction C and capable of storing two U-shaped staples S.

The staple storage portion 31 opens in the vertical direction B at the opening 31a provided on the upper surface 21e (FIG. 6) of the first distal-end portion 21a. The staple S is stored in the staple storage portion 31 through the opening 31a. The staple S is stored in the staple storage portion 31 with needle tips S1 of the staple S facing the upward side B1.

The staple storage portion 31 is formed in a rectangular shape with short sides extending in the axial direction A and long sides extending in the axial direction C in a plan view. In the staple S stored in the staple storage portion 31, the needle tips S1 at both ends are disposed in the axial direction C.

The linear movement member 32 is a member accommodated in a bottom part of the staple storage portion 31 and is movable in the vertical direction B in an internal space of the staple storage portion 31. The linear movement member 32 includes a recessed portion 32a that supports the staple S to the upward side B1. The staple S stored in the staple storage portion 31 is fitted into the recessed portion 32a.

A first pulley 34 and a second pulley 36 as the rotation member 33 are rotatably attached inside the stapling head 21. The first pulley 34 and the second pulley 36 rotate to move the linear movement member 32 in the vertical direction B. A distal end of the ejection operation wire 6 is coupled to the first pulley 34. When the ejection operation wire 6 is pulled in an arrow direction in FIG. 13, the first pulley 34 can be made to rotate.

The second pulley 36 is rotatably attached inside the stapling head 21, and the first pulley 34 is disposed on a distal-end side with respect to the second pulley 36. A rotation shaft 35 of the first pulley 34 and a rotation shaft 37 of the second pulley 36 extend in the axial direction C and are substantially parallel to the open-close rotation shaft 23 of the grasping portion 2. The first pulley 34 has a protruding portion 38, which supports the linear movement member 32 from the downward side B2, on the distal-end side.

The distal end of the ejection operation wire 6 is coupled to the upward side B1 above the rotation shaft 35 at the first pulley 34. The ejection operation wire 6 extends from the first pulley 34 to the ejection operation unit 270 shown in FIG. 1 via the second pulley 36 and passing through the second through hole 12. The reason for providing the second pulley 36 is to adjust a position of the ejection operation wire 6 for smoothly guiding it into the second through hole 12, and to reduce frictional resistance when the ejection operation wire 6 is guided into the second through hole 12. Therefore, the same effect can be obtained even when only the first pulley 34 is used as the rotation member 33 and a member having an R shape with a high degree of slidability and having reduced friction is provided in place of the second pulley 36.

Figure 14:
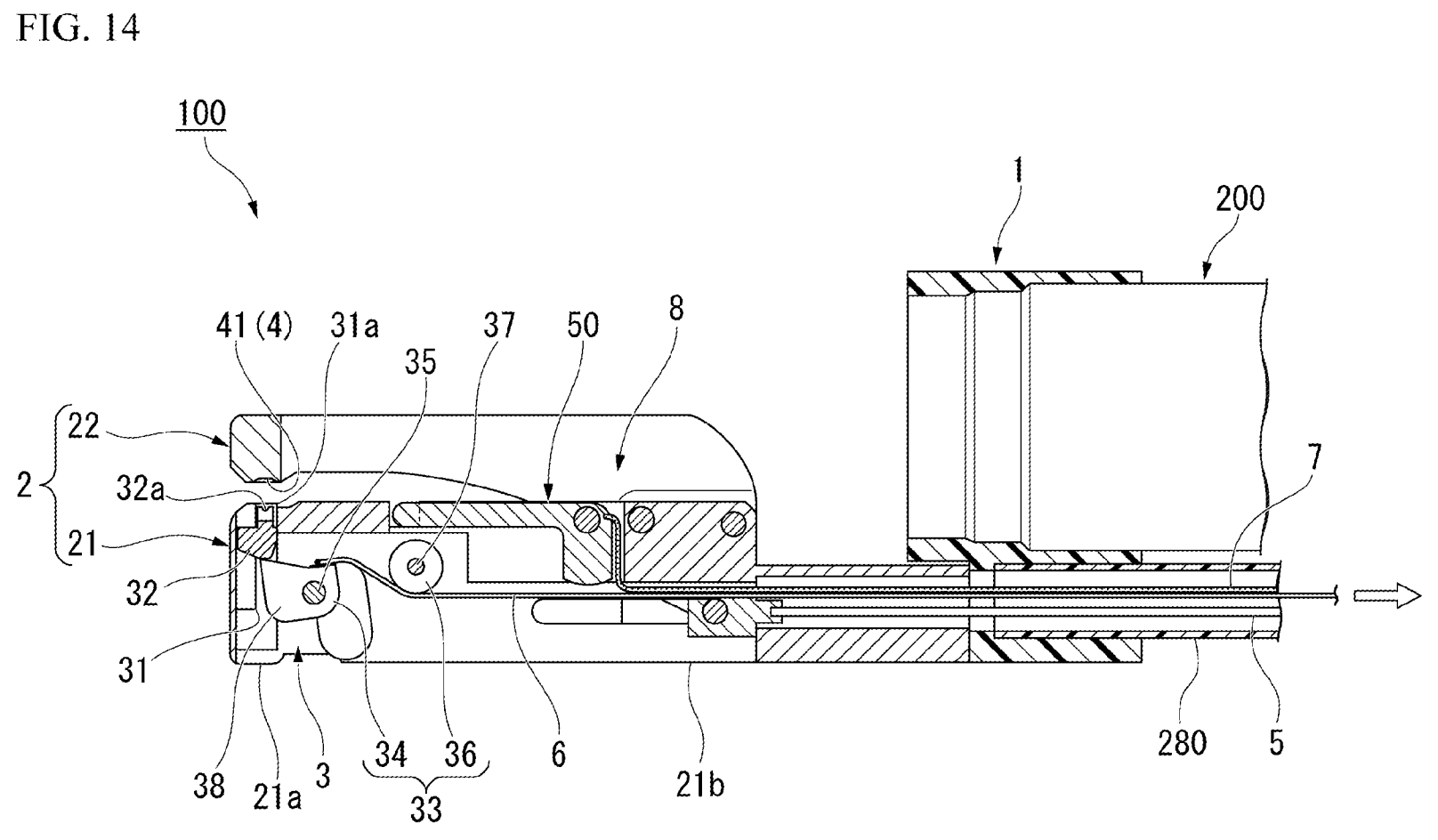

FIG. 14 is a cross-sectional view showing the grasping portion 2 in which the ejection operation wire 6 is pulled.

When the ejection operation wire 6 is pulled, an upper side of the first pulley 34 rotates to the proximal-end side around the rotation shaft 35, and a lower side of the first pulley 34 rotates to the distal-end side. As a result, the protruding portion 38 of the first pulley 34 pushes up the linear movement member 32 to the upward side B1, and the stored staple S is ejected from the opening 31*a* to the upward side B1.

The staple receiving portion 4 is provided on a lower surface of the second distal-end portion 22*c* of the anvil 22. A plurality of pockets 41 that can receive the staples S (FIG. 10) ejected from the staple ejection portion 3 are provided in the staple receiving portion 4. In the present embodiment, two U-shaped staples are ejected from the staple ejection portion 3. Therefore, four pockets 41 (FIG. 7) are provided in the staple receiving portion 4. When the grasping portion 2 is in the closed state, the opening 31*a* through which the staples S (FIG. 10) are ejected and the pockets 41 of the staple ejection portion 3 face each other in the vertical direction B.

[Operation of Medical Stapler 100]

Figure 15:
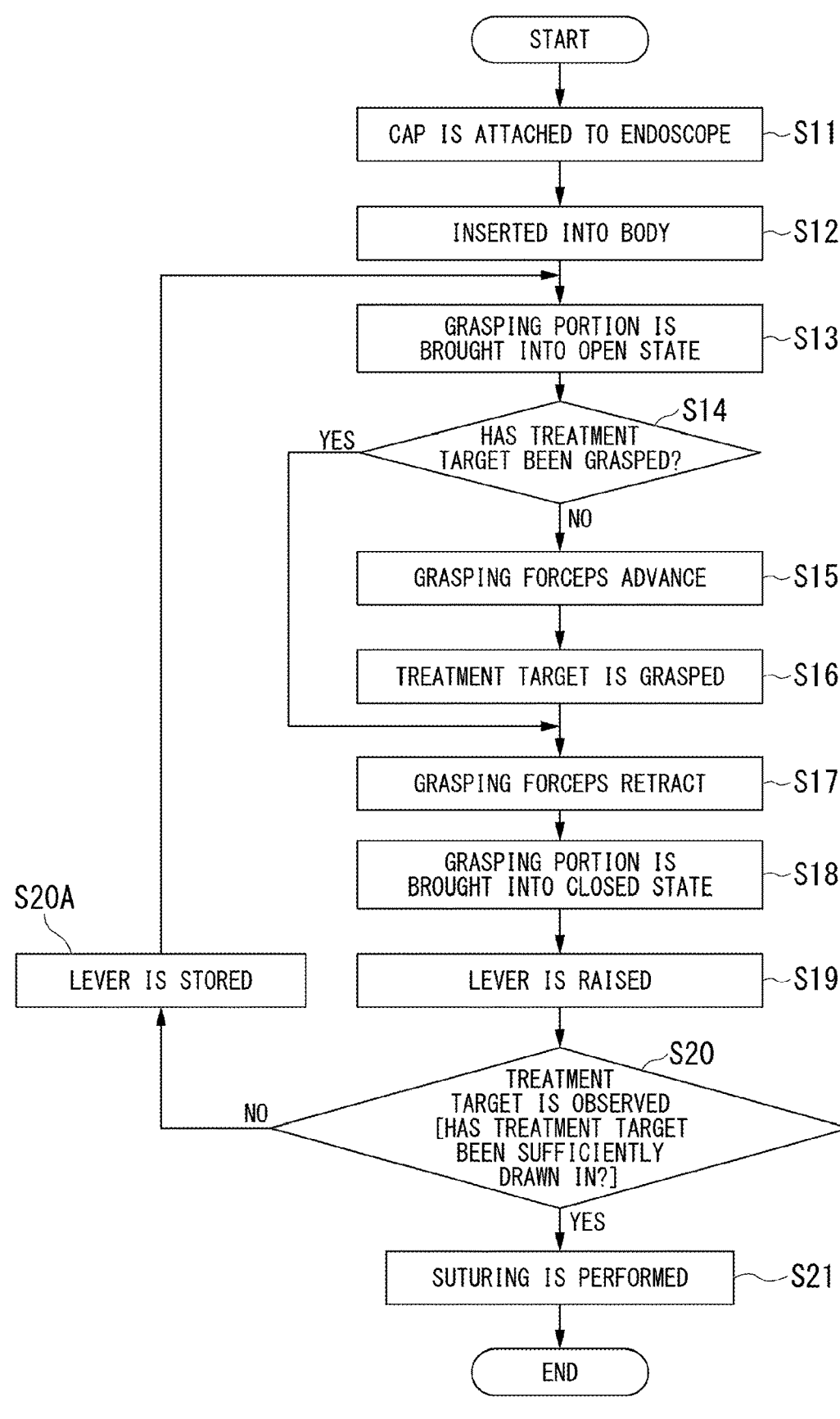
FIG. 15 is a flowchart showing a manipulation procedure performed by an operator using the medical stapler.

Next, an operation of the medical stapler 100 will be described. FIG. 15 is a flowchart showing a manipulation procedure performed by the operator using the medical stapler 100. FIGS. 16 to 21 are views showing an operation of the medical stapler 100.

Hereinafter, an operation of the medical stapler 100 will be described along the flowchart of FIG. 15 while referring to FIGS. 16 to 21.

First, the operator attaches the medical stapler 100 to the distal-end portion 211 of the endoscope 200 (attachment step S11). The operator inserts the endoscope 200 to which the medical stapler 100 is attached into the body (insertion step S12).

Next, the operator brings the distal-end portion 211 of the endoscope 200 to which the medical stapler 100 is attached closer to a treatment target T. The treatment target T is, for example, a part of a tissue inside the body.

The operator operates the open-close operation unit 250 shown in FIG. 1 to advance the open-close operation wire 5, thereby opening the anvil 22 to bring the grasping portion 2 into an open state (first open-close step S13). At this time, the lever 50 is in a stored state.

When the medical stapler 100 is inserted into the body for the first time, since the treatment target T is not grasped by the grasping forceps G (grasp ascertaining step S14: No), an advancing step S15 is subsequently performed.

After the grasping portion 2 is brought into the open state, the operator causes the grasping forceps G to protrude (advance) from the forceps port 214 and approach the treatment target T (advancing step S15). The operator can advance the grasping forceps G while ascertaining a position of the treatment target T through the visual space 25 using the imaging unit of the endoscope 200.

Figure 16:
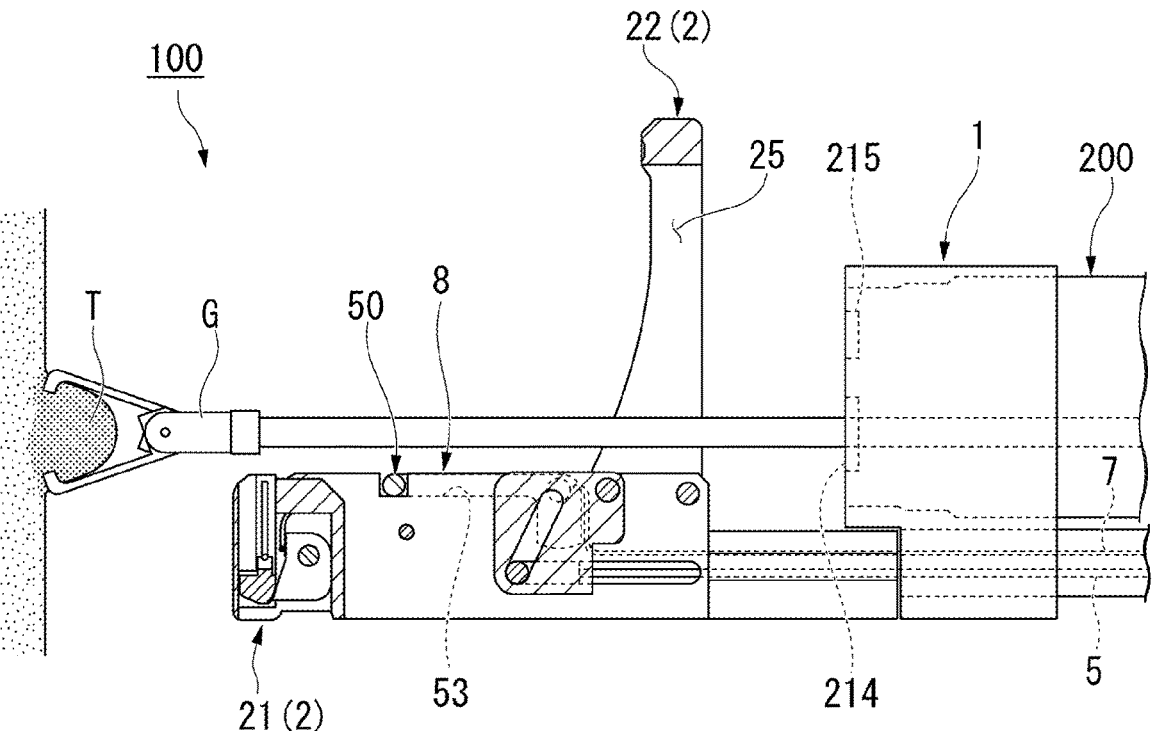
FIG. 16 is a view showing an operation of the medical stapler.

Since the lever 50 is in a stored state when the grasping portion 2 is in an open state, there is no protruding object on the stapling head 21 side and there is no obstacle to hinder observation. Therefore, the operator can satisfactorily observe the treatment target T through the visual space 25. As shown in FIG. 16, the operator grasps the treatment target T with the grasping forceps G (grasping step S16).

Figure 17:
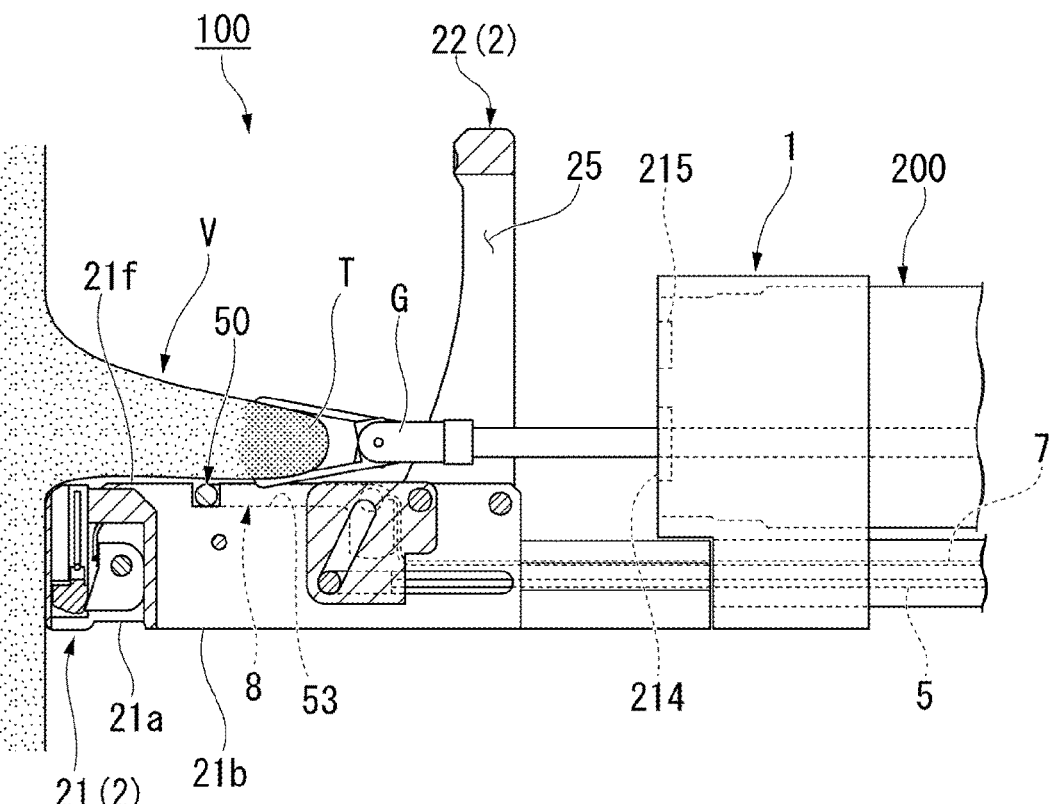
FIG. 17 is a view showing an operation of the medical stapler.

Next, as shown in FIG. 17, the operator retracts the grasping forceps G with the treatment target T grasped by the grasping forceps G (retracting step S17). For example, the operator retracts the grasping forceps G until a distal end of the grasping forceps G is positioned on the lever 50.

Figure 18:
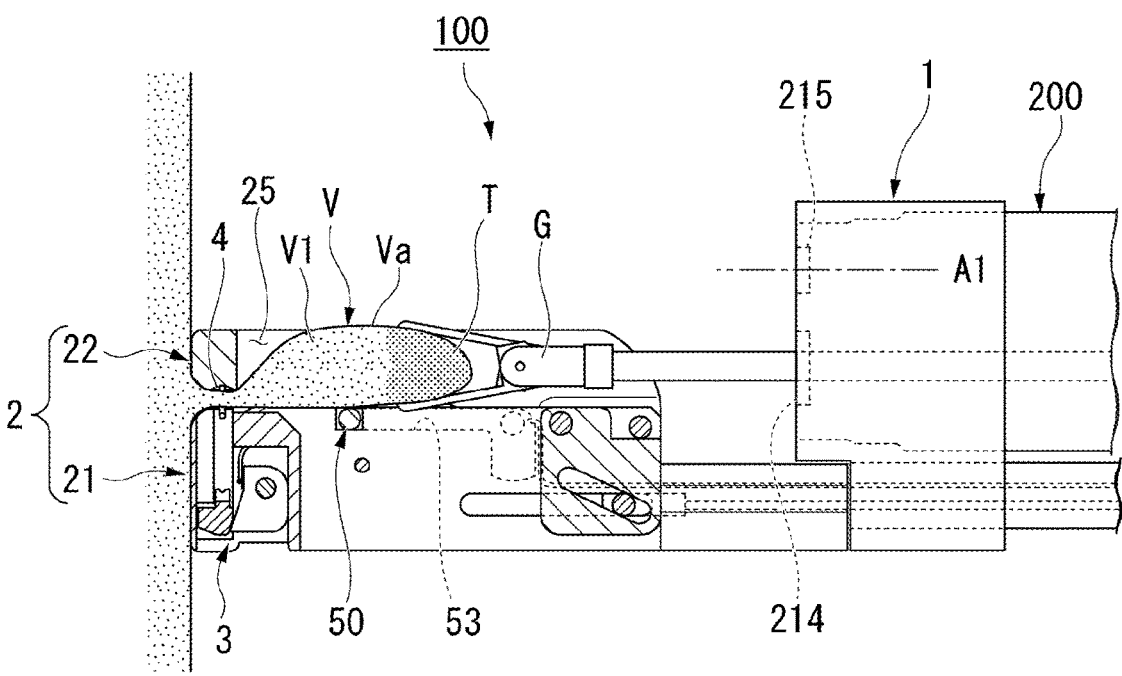
FIG. 18 is a view showing an operation of the medical stapler.

Next, the operator brings the grasping portion 2 into a closed state as shown in FIG. 18 by operating the open-close operation unit 250 shown in FIG. 1 to pull the open-close operation wire 5 (second open-close step S18). A tissue V containing the treatment target T grasped by the grasping forceps G is sandwiched between the staple ejection portion 3 of the stapling head 21 and the staple receiving portion 4 of the anvil 22.

When the grasping portion 2 is in the closed state, since a part of the tissue V of the treatment target T grasped by the grasping forceps G can be accommodated in the visual space 25 formed inside the anvil 22, there is an effect that the treatment target T sandwiched between the staple ejection portion 3 and the staple receiving portion 4 is less likely to lose.

When the grasping portion 2 is in the closed state, the optical axis A1 of the objective lens 215 of the imaging unit passes outside (the upward side B1) of the stapling head 21 and the anvil 22. Therefore, even when the grasping portion 2 is in the closed state, the operator can observe the tissue V containing the treatment target T using the imaging unit of the endoscope 200. At this time, the operator can observe a surface Va (a surface on a side opposite to the stapling head 21) of the tissue V containing the treatment target T using the imaging unit.

Figure 19:
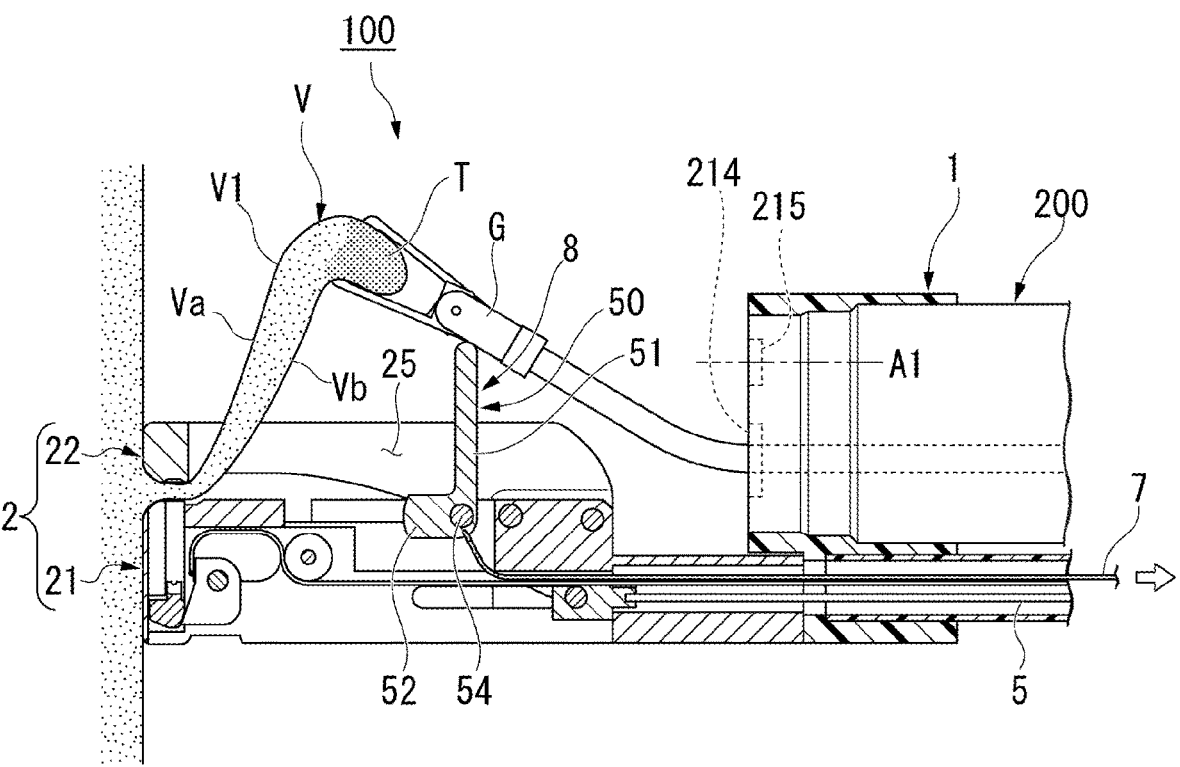
FIG. 19 is a view showing an operation of the medical stapler.

Next, the operator raises the lever 50 by operating the lever operation unit 260 shown in FIG. 1 to pull the lever operation wire 7 in a direction (rearward) indicated by the arrow shown in FIG. 19 while keeping the grasping portion 2 in the closed state (lever raising step S19).

Figure 20:
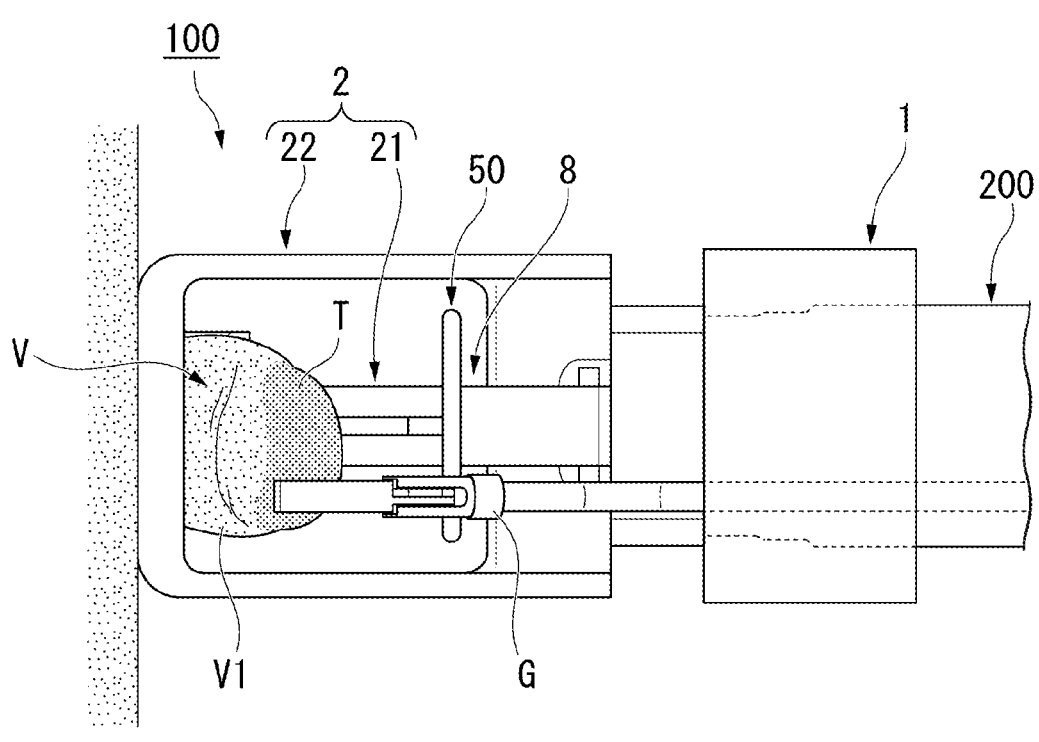
FIG. 20 is a view showing an operation of the medical stapler.

At this time, the grasping forceps G are pushed up by the lever 50 at the same time as the lever 50 rises, and the distal-end side of the grasping forceps G is lifted to the upward side B1. As shown in FIGS. 19 and 20, when the grasping forceps G are lifted by the lever 50, the tissue V containing the treatment target T grasped by the grasping forceps G is lifted to the upward side B1 with respect to the anvil 22 in a closed state. In this way, the tissue is turned up by raising the lever 50.

A back surface Vb (surface facing the stapling head 21) side of the tissue V containing the treatment target T lifted by the grasping forceps G faces the objective lens 215 in a direction of the optical axis A1 and is projected within a field of view showing the endoscope 200.

The operator can observe the back surface Vb of the tissue V containing the treatment target T lifted by the grasping forceps G and ascertain a position of the treatment target T using the imaging unit (observation step S20).

At this time, the operator can ascertain whether or not the entire treatment target T has been drawn into the visual space 25 using the grasping forceps G. That is, it can be ascertained whether or not the treatment target T is present at a suture position at which the staple ejection portion 3 and the staple receiving portion 4 face each other. The operator performs the next suturing step S21 after ascertaining that the treatment target T is not contained in a portion sandwiched between the staple ejection portion 3 and the staple receiving portion 4.

In the observation step 20 described above, if it is ascertained that the treatment target T is insufficiently drawn in and the treatment target T is present at the suture position, the operator advances the lever operation wire 7 to lower the lever 50 and store it in the lever accommodating groove 53 (lever storing step S20A).

Thereafter, the operator returns to the first open-close step S13 to bring the grasping portion 2 into an open state. The operator determines in step S14 to proceed to step S17 due to the state in which the treatment target T is grasped by the grasping forceps G (grasp ascertaining step S14: Yes), and further retracts the grasping forceps G (retracting step S17) while grasping the treatment target T to further draw the tissue V containing the treatment target T into the grasping portion 2. Thereafter, the grasping portion 2 is brought into a closed state to fix the tissue V (second open-close step S18), the treatment target T is lifted by raising the lever 50 upward with respect to the stapling head 21 (lever raising step S19), and the back surface side of the treatment target T is observed again (observation step S20). The operator performs steps S13 to S20 until it is ascertained that the treatment target T is not contained in the portion sandwiched between the staple ejection portion 3 and the staple receiving portion 4. At this time, steps S15 and S16 are skipped. The operator draws in the treatment target T to the proximal-end side with respect to the staple ejection position. After ascertaining that the treatment target T is not contained in the portion sandwiched between the staple ejection portion 3 and the staple receiving portion 4, the operator performs the next operation.

Next, in a state in which a healthy tissue V1 around the treatment target T at a portion that does not contain the treatment target T among the tissue V pulled by the grasping forceps G is sandwiched between the staple ejection portion 3 and the staple receiving portion 4, the operator operates the ejection operation unit 270 to pull the ejection operation wire 6. Therefore, the staple S stored in the staple ejection portion 3 is ejected toward the staple receiving portion 4. At this time, the staple S may be ejected from the stapling head 21 a plurality of times. The needle tips S1 of the staple S penetrate the tissue V1 around the treatment target T and are bent by coming into contact with the pockets 41 of the staple receiving portion 4. As a result, the tissue V containing the treatment target T is sutured in a state in which the treatment target T is entirely contained. Therefore, the entire treatment target T is sutured (suturing step S21).

Figure 21:
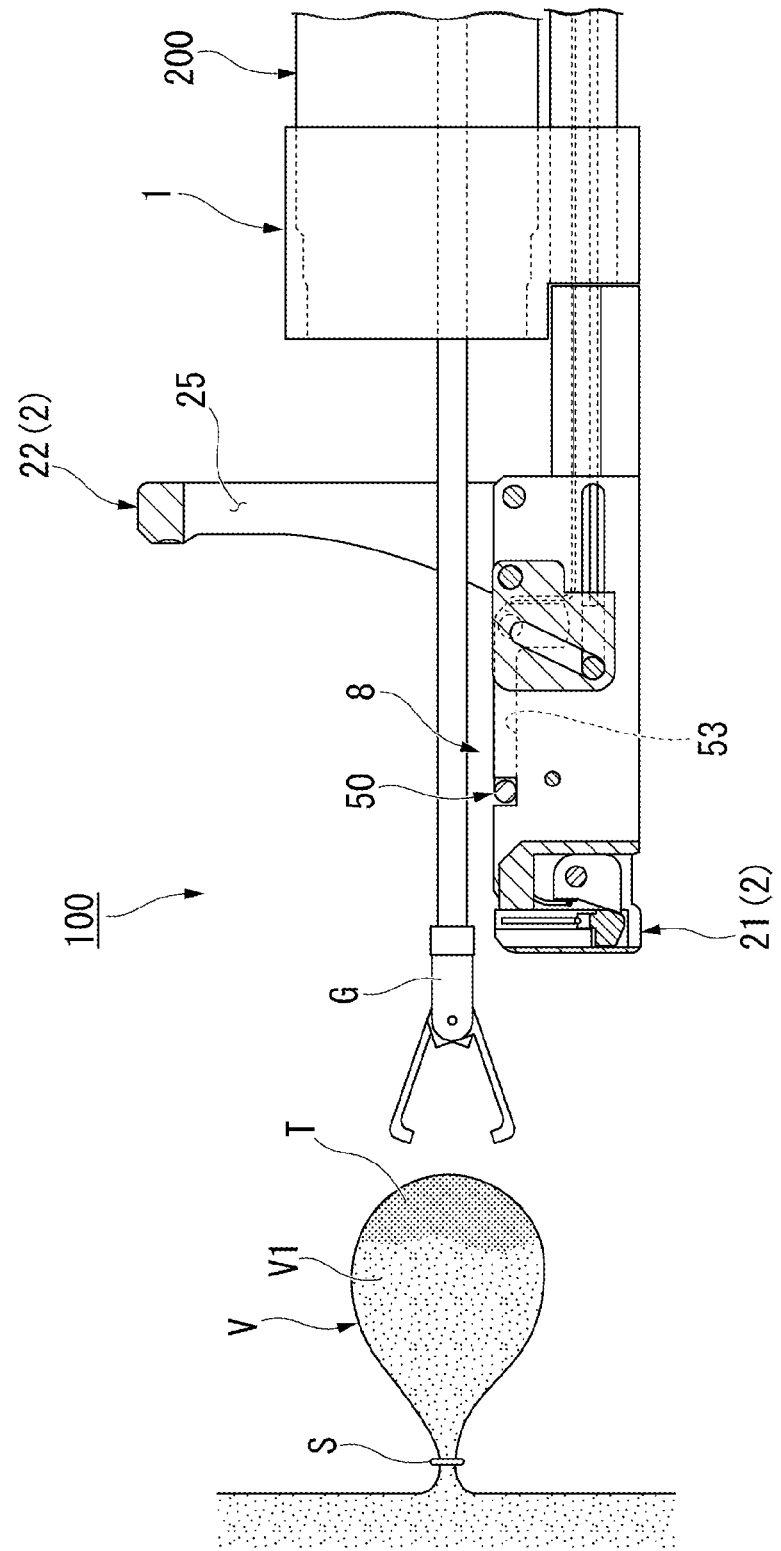
FIG. 21 is a view showing an operation of the medical stapler.

Next, as shown in FIG. 21, the operator operates the open-close operation unit 250 shown in FIG. 1 to bring the grasping portion 2 into an open state again. The operator opens the grasping forceps G to release the grasp on the treatment target T, thereby completing the suturing treatment. Thereafter, the operator removes the medical stapler 100 and endoscope 200 from the inside of the body.

According to the medical stapler 100 of the present embodiment, when the treatment target T grasped by the grasping forceps G is lifted to the upward side B1 by the lever 50, a state of the back surface (surface facing the stapling head 21) of the treatment target T can be visually observed using the imaging unit. Therefore, the treatment target T can be sufficiently drawn into the grasping portion 2 by the grasping forceps G while ascertaining the suture position. The operator can perform suturing on a circumference of the treatment target T, that is, in a state of containing the entire treatment target T. Therefore, the treatment target T can be completely excised, and a treatment effect can be improved.

According to the medical stapler 100 of the present embodiment, since an insertion diameter of the medical stapler 100 with the grasping portion 2 in a closed state is substantially the same as that of the distal-end portion 211 of the endoscope 200, it can be easily inserted into the body such as the digestive tract. Also, even if the grasping portion 2 of the medical stapler 100 is in an open state, the operator can observe the treatment target T using the imaging unit of the endoscope 200 and can treat the treatment target T by causing the grasping forceps G to protrude from the forceps port 214.

While the first embodiment of the present disclosure has been described in detail as above with reference to the drawings, the specific configurations are not limited to the embodiment and may include design changes or the like within a range not departing from the gist of the present invention. Also, the components shown in the embodiment and modified examples described above can be configured by appropriately combining them.

For example, a structure of the lever portion 8 is not limited to the aspect of the first embodiment. Hereinafter, modified examples of the lever portion 8 will be described. Further, in the following description, components that are common to those already described will be denoted by the same reference signs and duplicate description will be omitted.

Modified Example 1

For example, the lever rotation shaft 54 of the lever 50 has been provided separately from the open-close rotation shaft 23 of the anvil 22 in the first embodiment described above, but a configuration of the lever portion 8 is not limited thereto.

Figure 22:
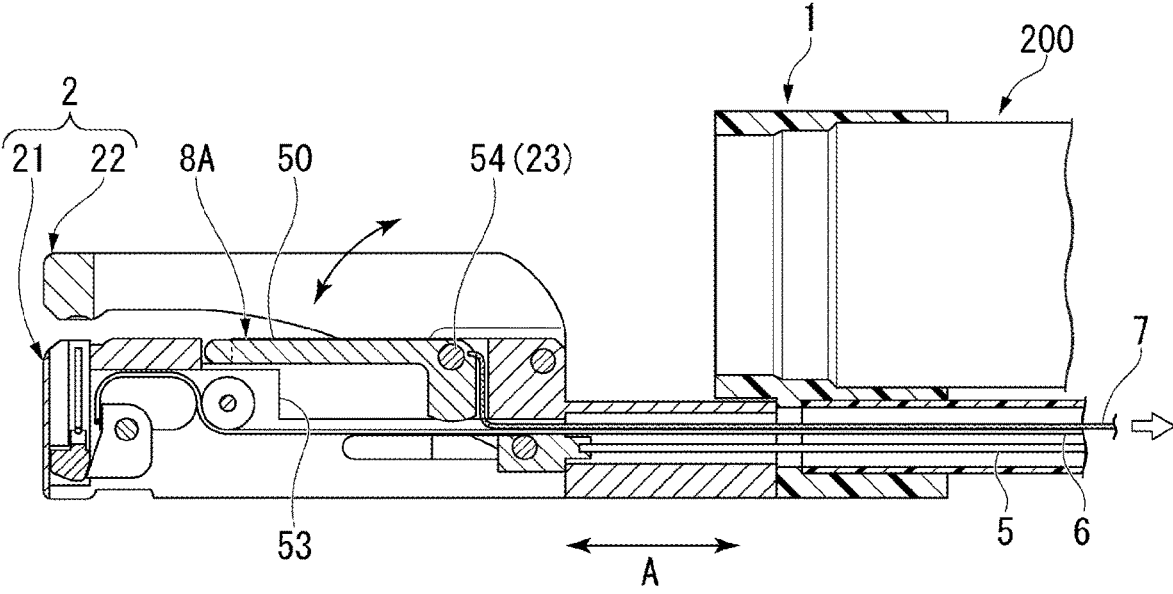
FIG. 22 is a cross-sectional view showing a lever portion in modified example 1 of a first embodiment.

FIG. 22 is a cross-sectional view showing the lever portion 8A in modified example 1 of the first embodiment.

Modified example 1 of the first embodiment will be described with reference to FIG. 22.

As shown in FIG. 22, in the lever portion 8A of modified example 1, the lever rotation shaft 54 is provided coaxially with the open-close rotation shaft 23 of the anvil 22. As long as rotation of the lever 50 and an open-close operation of the anvil 22 can be operated independently, the lever rotation shaft 54 and the open-close rotation shaft 23 may be formed of the same member.

According to the configuration of modified example 1, when the lever rotation shaft 54 and the open-close rotation shaft 23 are provided coaxially, a length of the lever 50 in the axial direction A can be increased. Therefore, since a height of the lever 50 when it is raised can be increased, the grasping forceps G can be lifted higher to the upward side B1. Therefore, since the tissue V containing the treatment target T grasped by the grasping forceps G can be further turned up, it becomes easier to see the back surface Vb side of the tissue V and makes it easier to ascertain the suture position.

Also, since the lever rotation shaft 54 and the open-close rotation shaft 23 can be formed of the same member, the number of parts is reduced, and therefore it is possible to make assembly easier and reduce costs.

Modified Example 2

For example, a configuration in which the rotation direction F of the lever 50 is the same as the open-close direction R of the anvil 22 has been described in the first embodiment, but a rotation direction of the lever 50 is not limited thereto.

Figure 23A:
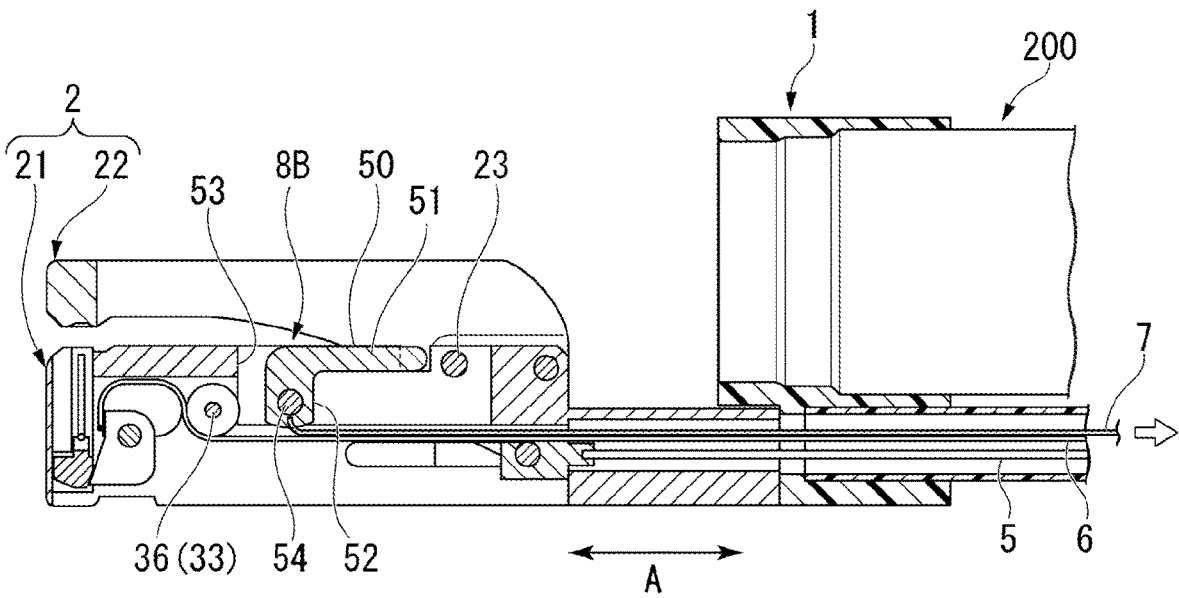
FIG. 23A is a cross-sectional view showing a lever portion of modified example 2 in the first embodiment.
Figure 23B:
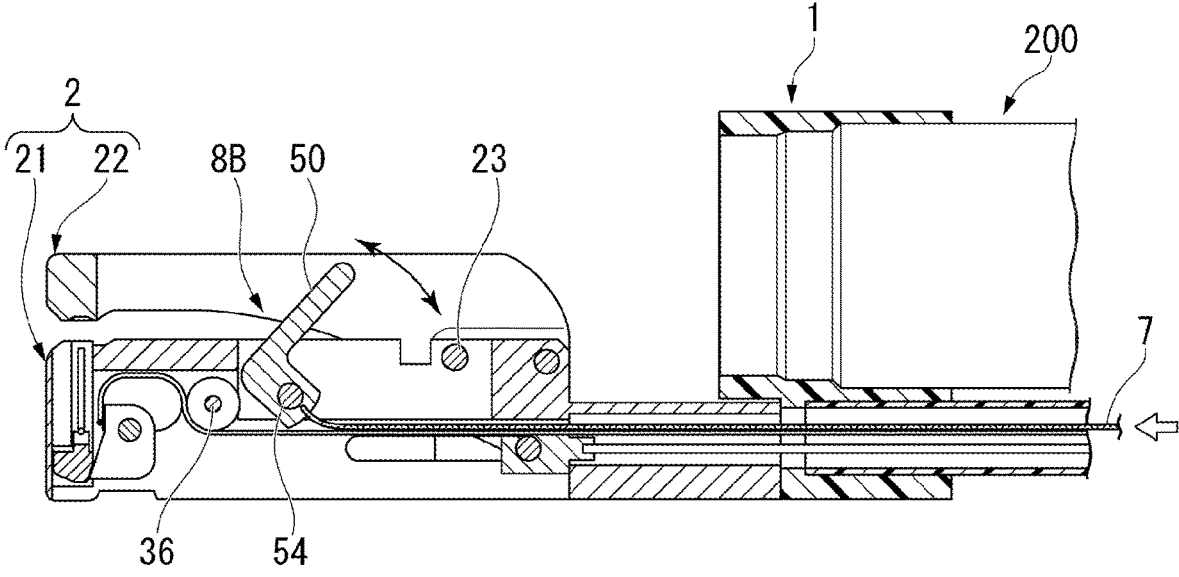
FIG. 23B is a cross-sectional view showing the lever portion of modified example 2 in the first embodiment.

FIGS. 23A and 23B are cross-sectional views showing a lever portion 8B of modified example 2 of the first embodiment.

Modified example 2 of the first embodiment will be described with reference to FIGS. 23A and 23B.

As shown in FIG. 23A, in the lever portion 8B of modified example 2, the lever 50 is attached in a direction opposite to that in the first embodiment in the axial direction A.

The lever rotation shaft 54 in modified example 2 is disposed near the rotation shaft 37 of the second pulley 36 in the staple ejection portion 3 at a position separated to the front from the open-close rotation shaft 23. The lever rotation shaft 54 is positioned behind the rotation shaft 37.

The lever 50 is accommodated in the lever accommodating groove 53 in an orientation in which the main body portion 51 is directed rearward with respect to the lever rotation shaft 54 and the support portion 52. The lever operation wire 7 is coupled to the support portion 52 positioned forward of the main body portion 51 of the lever 50 in an orientation in which the lever 50 is accommodated in the lever accommodating groove 53.

As shown in FIG. 23B, when the lever operation wire 7 is pulled backward when the grasping portion 2 is in the closed state, the lever 50 rises while rotating forward around an axis of the lever rotation shaft 54, and protrudes to the upward side B1 with respect to the stapling head 21. At this time, for example, the lever 50 can be raised until it assumes a vertical orientation. In this way, it is possible to lift the tissue V and the grasping forceps G.

According to modified example 2, it is possible to lift the tissue V and the grasping forceps G to the upward side B1 while an upper surface side of the lever 50 remains in contact with the tissue V. Therefore, it is possible to ascertain the back surface side of the tissue V more easily.

Modified Example 3

For example, a configuration in which the lever 50 rises when the lever operation wire 7 is pulled backward has been described in the first embodiment described above, but a configuration of the lever portion 8 is not limited thereto.

Figure 24A:
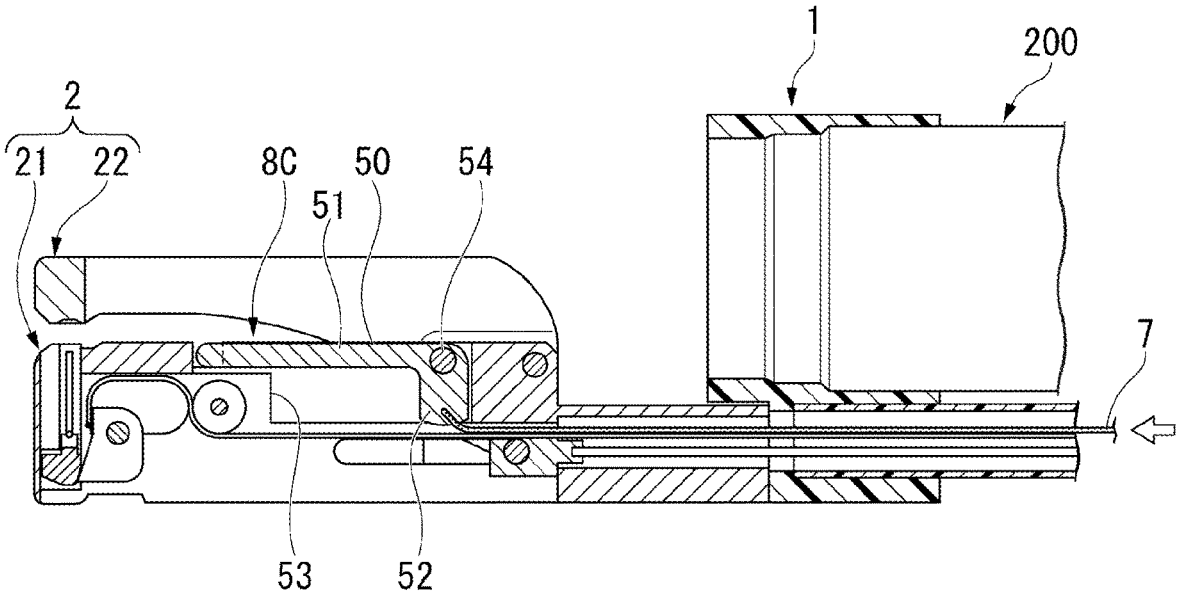
FIG. 24A is a cross-sectional view showing a lever portion of modified example 3 in the first embodiment.
Figure 24B:
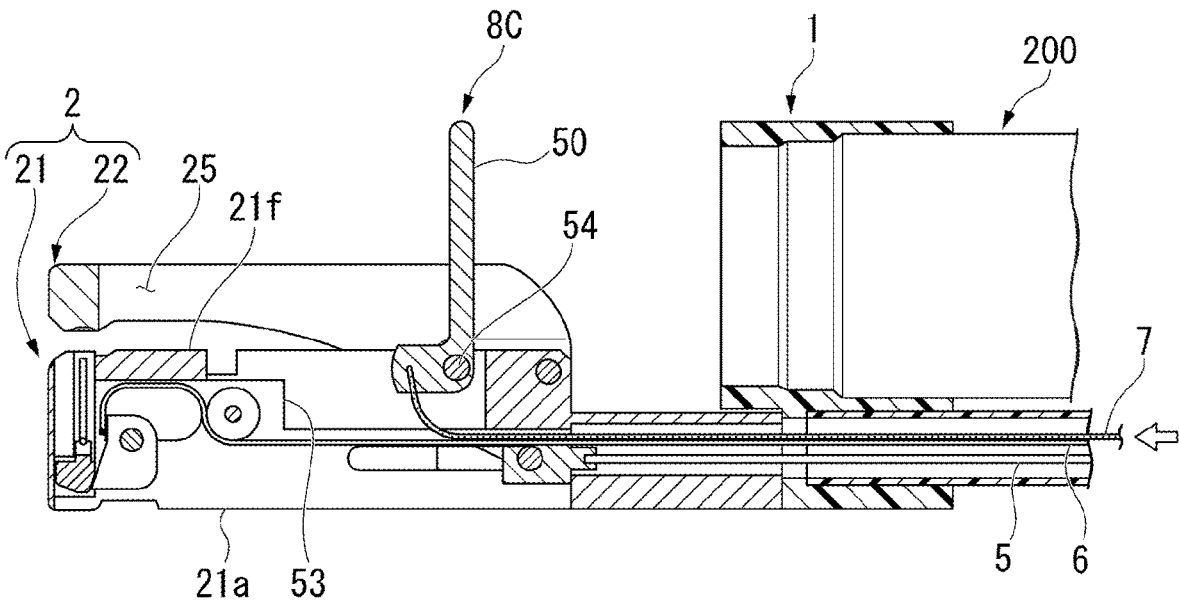
FIG. 24B is a cross-sectional view showing the lever portion of modified example 3 in the first embodiment.

FIGS. 24A and 24B are cross-sectional views showing a lever portion 8C of modified example 3 of the first embodiment.

Modified example 3 of the first embodiment will be described with reference to FIGS. 24A and 24B.

As shown in FIGS. 24A and 24B, the lever portion 8C of modified example 3 is configured to rise when the lever operation wire 7 advances. As shown in FIG. 24A, when the lever 50 is in a state of being accommodated, the support portion 52 of the lever 50 extends to the downward side B2, and the distal end 7a of the lever operation wire 7 is coupled to a lower end (one end) side of the support portion 52.

When the lever operation wire 7 advances as shown in FIG. 24B, the lever 50 rotates around an axis of the lever rotation shaft 54 so that the support portion 52 is pushed forward, and the main body portion 51 rises rearward. In this way, when the lever operation wire 7 advances, it is possible to raise the lever 50 higher than the stapling head 21.

According to the configuration of modified example 3, since the gap 9 (FIG. 10) for causing the distal end 7a of the lever operation wire 7 to enter is not required in the lever accommodating groove 53, it is possible to increase a length of the lever 50 in the axial direction A.

Modified Example 4

For example, the T-shaped lever 50 in a plan view has been used in the first embodiment described above, but a shape of the lever 50 is not limited thereto.

Figure 25:
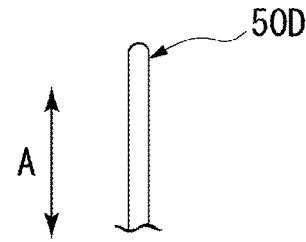
FIG. 25 is a plan view showing a shape of a lever of modified example 4 in the first embodiment.

FIG. 25 is a plan view showing a shape of the lever 50D of modified example 4 in the first embodiment. Modified example 4 of the first embodiment will be described with reference to FIG. 25.

As shown in FIG. 25, the lever 50D of modified example 4 has an I shape in a plan view extending in the axial direction A when it is in a state of being stored in the lever accommodating groove 53, for example, as shown in FIG. 6.

According to modified example 4, when the lever 50D is made to have an I shape in a plan view extending in the axial direction A, a part structure is simplified, and thereby manufacturing is facilitated and costs can be reduced. Also, when the lever 50D has lifted the tissue V and the grasping forceps G at the time of rising, a portion hindering a visual field from the imaging unit reduces, thereby it is easy to observe the tissue V.

While the first embodiment and modified examples 1 to 4 of the present disclosure have been described in detail with reference to the drawings, the specific configurations are not limited to the embodiment and modified examples and may include design changes or the like within a range not departing from the gist of the present invention. Also, the components shown in the first embodiment and modified examples 1 to 4 described above can be configured by appropriately combining them.

Second Embodiment

Next, a medical stapler 102 of a second embodiment will be described with reference to FIGS. 26 to 28C. In the following description, components that are common to those already described will be denoted by the same reference signs and duplicate description will be omitted.

[Medical Stapler 102]

The medical stapler 102 according to the second embodiment is different in function and structure of the lever portion compared to the medical stapler 100 according to the first embodiment. In the first embodiment described above, the structure has been such that the tissue V and the grasping forceps G are lifted upward by raising the lever portion 8, but a structure of the lever portion is not limited thereto.

Figure 26:
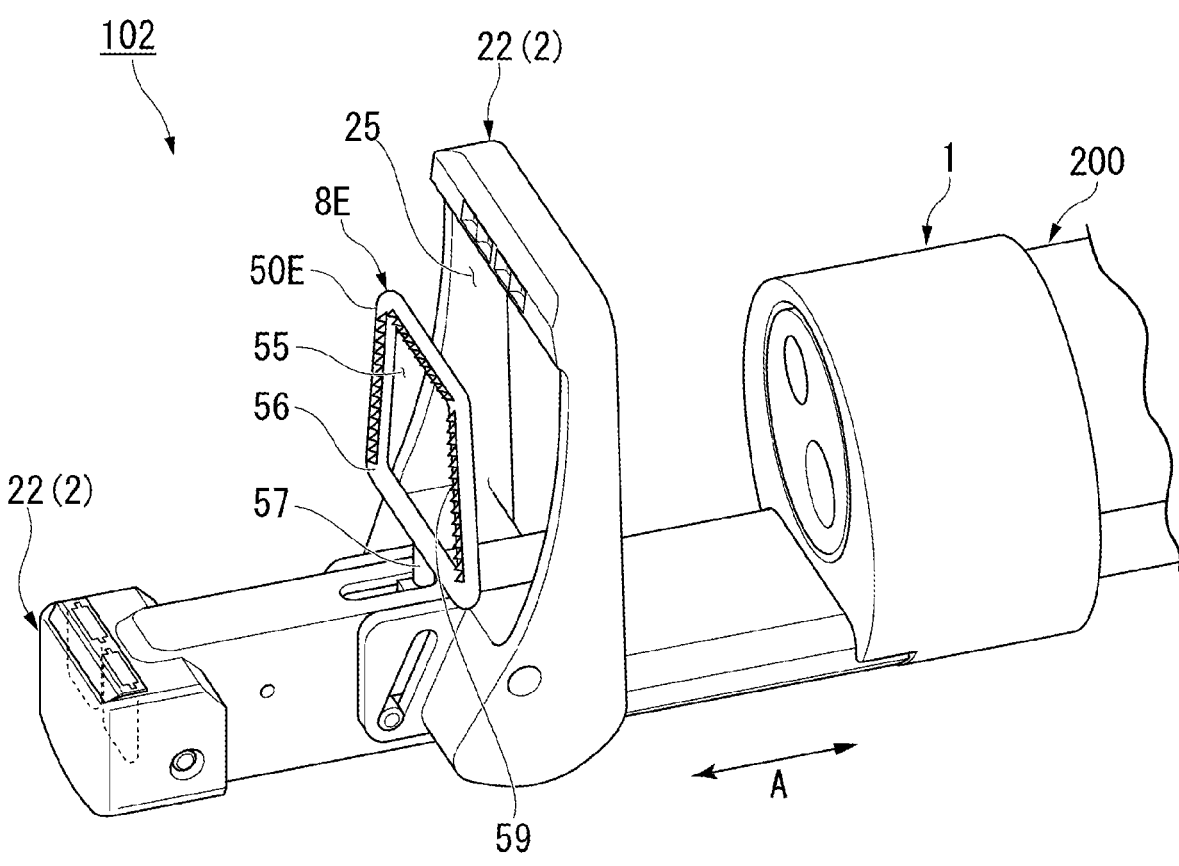
FIG. 26 is a perspective view showing a structure of a medical stapler of a second embodiment.
Figure 27:
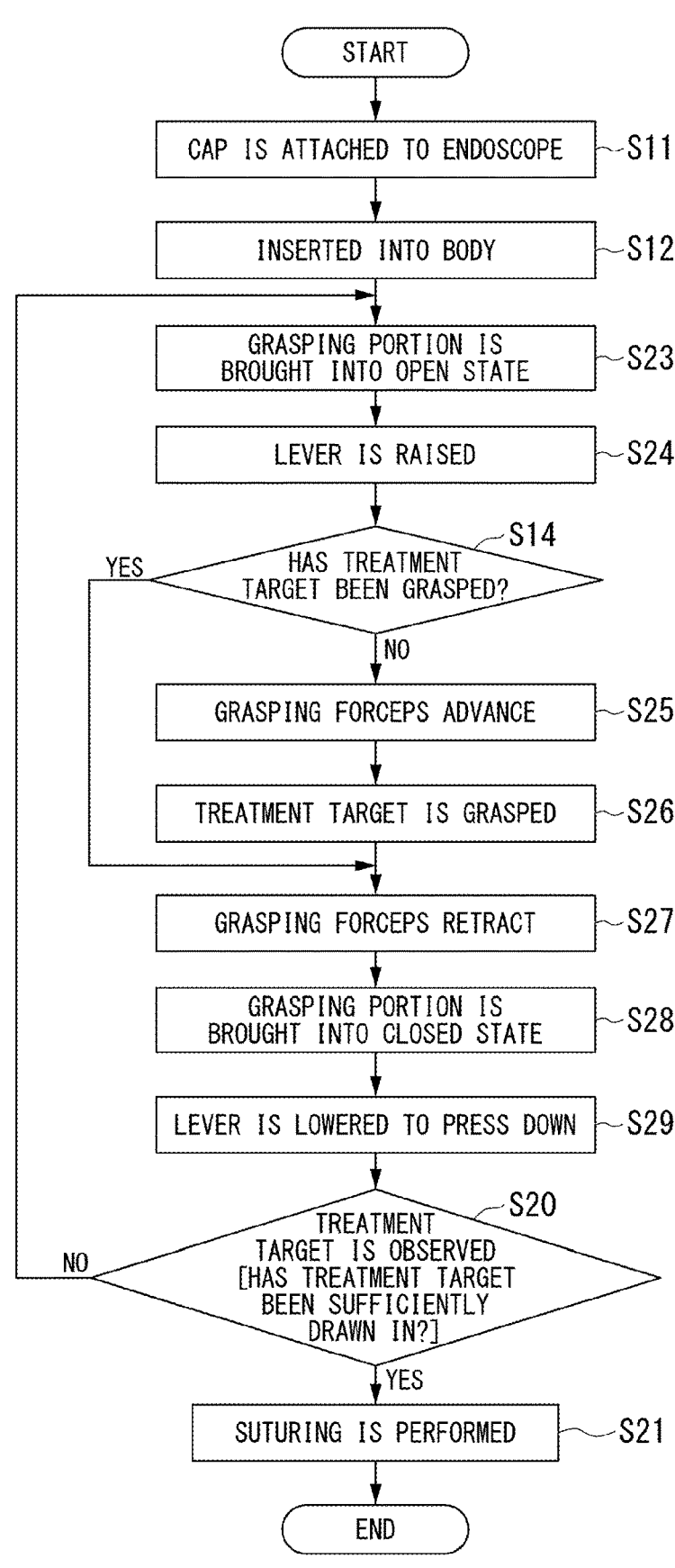
FIG. 27 is a flowchart showing a manipulation procedure using the medical stapler of the second embodiment.
Figure 28A:
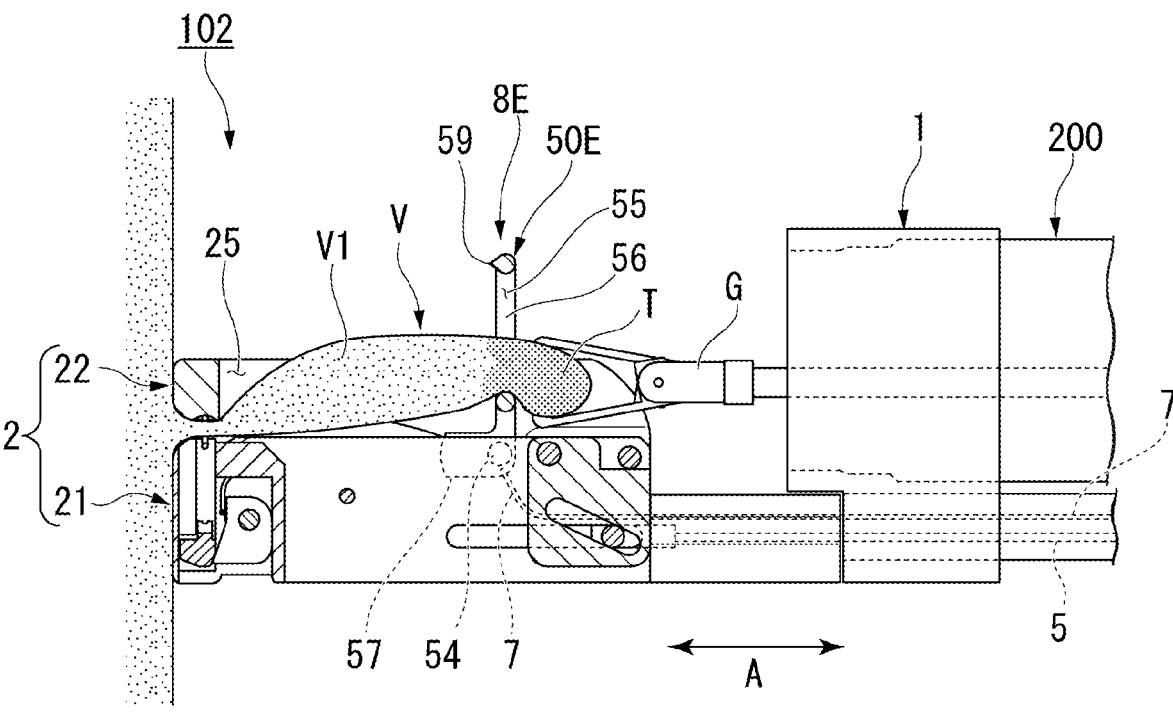
FIG. 28A is a view showing an operation of the medical stapler of the second embodiment.
Figure 28B:
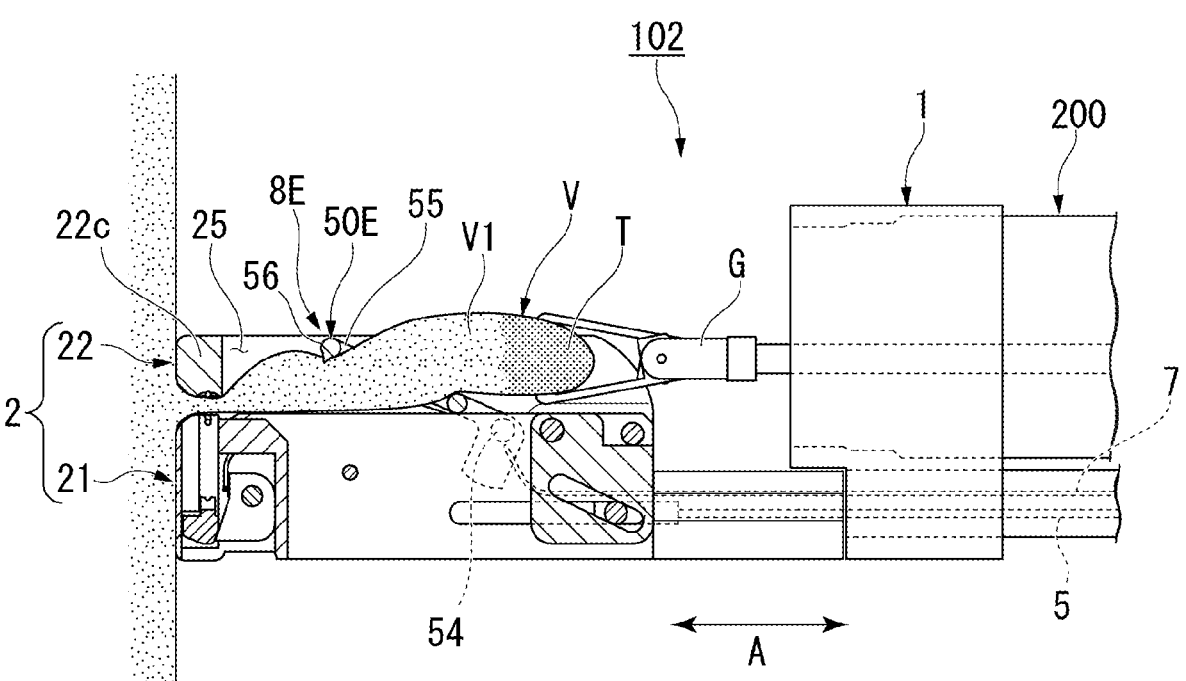
FIG. 28B is a view showing an operation of the medical stapler of the second embodiment.
Figure 28C:
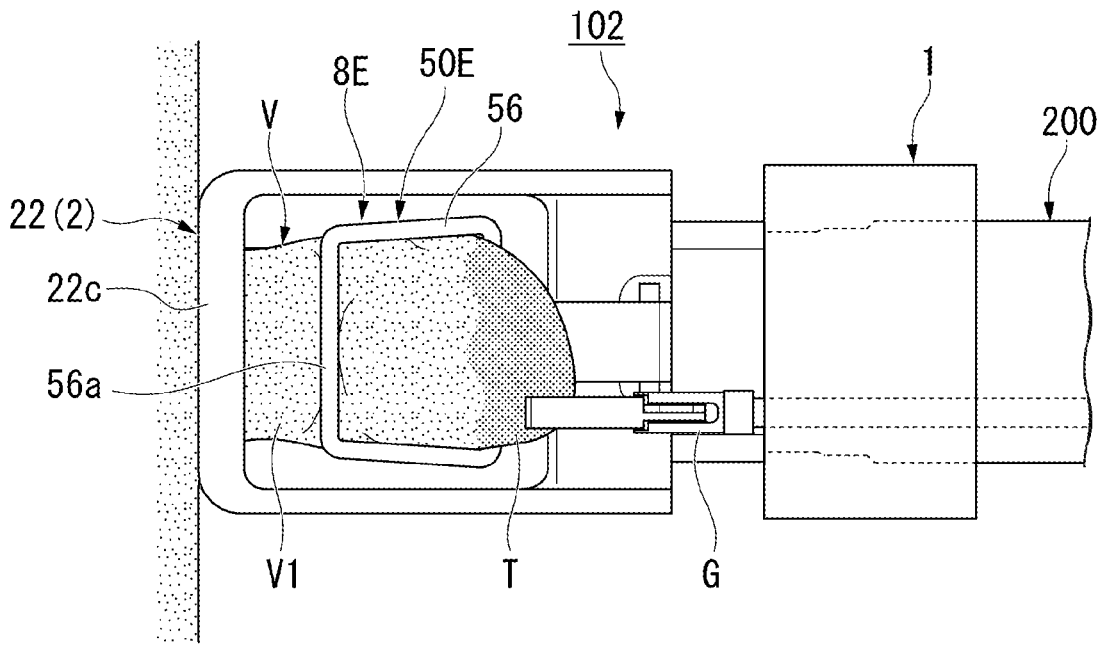
FIG. 28C is a view showing an operation of the medical stapler of the second embodiment.

FIG. 26 is a perspective view showing a structure of the medical stapler 102 of the second embodiment. FIG. 27 is a flowchart showing a manipulation procedure using the medical stapler 102 of the second embodiment. FIGS. 28A to 28C are views showing an operation of the medical stapler 102 of the second embodiment.

As shown in FIG. 28B, the medical stapler 102 of the present embodiment is configured to be able to press down a tissue V drawn in by grasping forceps G from above.

Specifically, the medical stapler 102 includes a lever portion 8E shown in FIG. 26. The lever portion 8E is rotatable independently of an open-close operation of an anvil 22. The lever portion 8E has a lever 50E that has a trapezoidal frame shape in a plan view.

The lever 50E is smaller in size in a plan view than the anvil 22 and is formed in a size to be accommodated within a visual space 25. Also, the lever 50E is constituted by a frame-shaped pressing portion 56 that forms a visual space (second visual space) 55 that is smaller than the visual space 25 of the anvil 22, and a connection portion 57 that is connected to a lever rotation shaft 54 (FIG. 28A).

The pressing portion 56 has, for example, a trapezoidal shape in a plan view, and a dimension in a width direction gradually decreases as it goes from the connection portion 57 side to a distal-end side. The visual space 55 defined and formed by the frame-shaped pressing portion 56 has a size that allows the grasping forceps G and a treatment target T grasped by the grasping forceps G to pass therethrough as shown in FIG. 28A.

In the present embodiment, as shown in FIG. 26, a slip stopper 59 with respect to the tissue V is formed on a surface on a lower side of the pressing portion 56, but the present disclosure is not limited thereto. The slip stopper 59 is not necessarily a necessary component, but when it is provided, the tissue V can be more reliably pressed by the pressing portion 56. A range in which the slip stopper 59 is provided is not limited to the range shown in the drawings.

[Operation of Medical Stapler 102]

Hereinafter, an operation of the medical stapler 102 of the second embodiment will be described along the flowchart of FIG. 27 while referring to FIGS. 26 and 28A to 28C. Operations the same as those of the medical stapler 100 of the first embodiment will be denoted by the same reference signs, and duplicate description thereof will be omitted.

When the medical stapler 102 of the present embodiment is used, the operator operates an open-close operation wire 5 to open the anvil 22 and bring a grasping portion 2 into an open state (first open-close step S23), and operates a lever operation wire 7 to raise the lever 50E of the lever portion 8E upward (lever raising step S24). In this state (the state shown in FIG. 26), the visual space 25 of the anvil 22 and the visual space 55 of the lever 50E communicate with each other in an axial direction A.

Next, the grasping forceps G advance toward the treatment target T through the visual space 25 of the anvil 22 in an open state and the visual space 55 of the lever 50E in which the grasping forceps G are raised (advancing step S25).

Next, the operator grasps the treatment target T with the grasping forceps G (grasping step S26), and retracts the grasping forceps G to the rear (retracting step S27). At this time, the grasping forceps G may be retracted to the rear of the anvil 22 and the lever 50E through the visual spaces 25 and 55.

Next, as shown in FIG. 28A, the operator brings the grasping portion 2 into a closed state (second open-close step S28), and grasps the tissue V with the anvil 22 and a stapling head 21.

Next, as shown in FIG. 28B, the operator lowers the lever 50E and presses down the tissue V grasped by the grasping portion 2 from above (pressing step S29). As shown in FIGS. 28B and 28C, the lever 50E is capable of pressing down on a portion on a rear side (endoscope 200 side) with respect to a portion grasped by the grasping portion 2. After ascertaining that substantially the entire of the treatment target T has been drawn in, a suturing treatment is performed.

According to the configuration of the second embodiment, of the tissue V containing the treatment target T drawn into the visual space 25 by the grasping forceps G, a region close to the portion grasped by the grasping portion 2 can be pressed down from above. If the tissue V grasped by the grasping forceps G has a thickness, although there has been cases in which the tissue V itself becomes a disturbance and makes it difficult to ascertain the suture position, since a second distal-end portion 22c of the anvil 22 is not hidden by the tissue V when the region close to the tissue V grasped by the grasping portion 2 is further pressed down from above by the lever 50E, it is made easier to ascertain the suture position from above the tissue V using the imaging unit.

In the present embodiment, the lever portion 8E is configured to be rotatable independently of the anvil 22, but the lever portion 8E may be configured to rotate in conjunction with an open-close operation of the anvil 22.

Modified Example 5

In the second embodiment, the pressing portion 56 of the lever 50E is formed in a trapezoidal shape in a plan view, and a distal-end portion 56a (FIG. 28C) has a narrowest shape, but a shape thereof is not limited thereto.

Figure 29A:
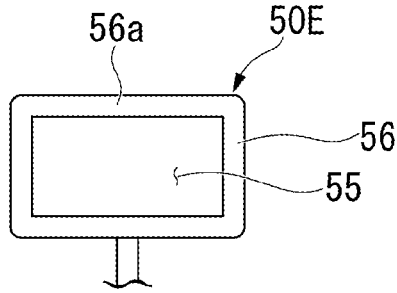
FIG. 29A is a plan view showing a lever of modified example 1 in the second embodiment.

FIG. 29A is a plan view showing a lever 50E of modified example 1 in the second embodiment.

As the lever 50E shown in FIG. 29A, a shape of a pressing portion 56 in a plan view may be formed in a rectangular frame shape having a length in a width direction. According to this shape, since a width dimension does not change from a proximal end to a distal end of the lever 50E, manufacturing is facilitated. Also, since the width of the distal-end portion 56a is large, the tissue V can be pressed down over a wide range. Further, since the visual space 55 that is long in the width direction can be formed, for example, the tissue V that has extended in the width direction by being grasped by the grasping forceps G can be easily passed therethrough, and both sides of the tissue V grasped by the grasping portion 2 can be more easily ascertained.

Modified Example 6

Figure 29B:
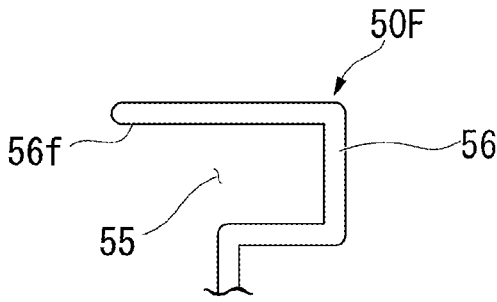
FIG. 29B is a plan view showing a lever of modified example 2 in the second embodiment.

In the second embodiment, the pressing portion 56 of the lever 50E has been formed in a frame shape that is closed in a circumferential direction, but a shape thereof is not limited thereto. FIG. 29B is a plan view showing a lever 50F of modified example 2 in the second embodiment.

As in the lever 50F shown in FIG. 29B, a pressing portion 56 formed by bending a rod-shaped body may be used. The pressing portion 56 of modified example 2 does not have a closed shape in the circumferential direction as in the second embodiment described above, but has an opening 56f formed in a part thereof. The opening 56f is formed on one side of the pressing portion 56 in a width direction. Since a part of the visual space 55 formed inside the pressing portion 56 is open, when the tissue V grasped by the grasping forceps G is passed through the visual space 55, the tissue V is less likely to come into contact with the pressing portion 56. Therefore, the grasping forceps G can be smoothly retracted and the tissue V can be smoothly drawn in.

While the second embodiment of the present disclosure has been described in detail as above with reference to the drawings, the specific configurations are not limited to the embodiment and may include design changes or the like within a range not departing from the gist of the present invention. Also, it is possible to configure the second embodiment by appropriately combining the components shown in the above-described first embodiment and the components shown in the modified examples of the first embodiment.

Third Embodiment

Next, a medical stapler 103 of a third embodiment will be described with reference to FIGS. 30 to 33D. In the following description, components that are common to those already described will be denoted by the same reference signs and duplicate description will be omitted.

[Medical Stapler 103]

The medical stapler 103 according to the third embodiment is different in function and structure of the lever portion compared to the medical staplers 100 and 102 according to the first and second embodiments. In the first embodiment described above, the structure has been such that the tissue V and the grasping forceps G are lifted upward by raising the lever portion 8, but a structure of the lever portion is not limited thereto.

Figure 30:
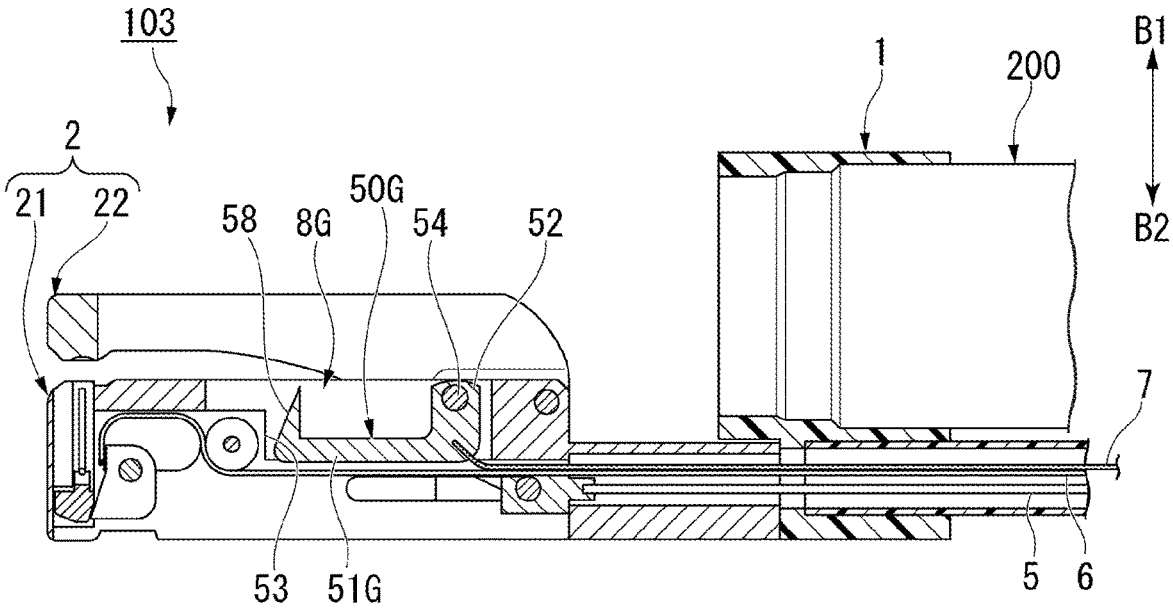
FIG. 30 is a cross-sectional view showing a structure of a medical stapler of a third embodiment.
Figure 31:
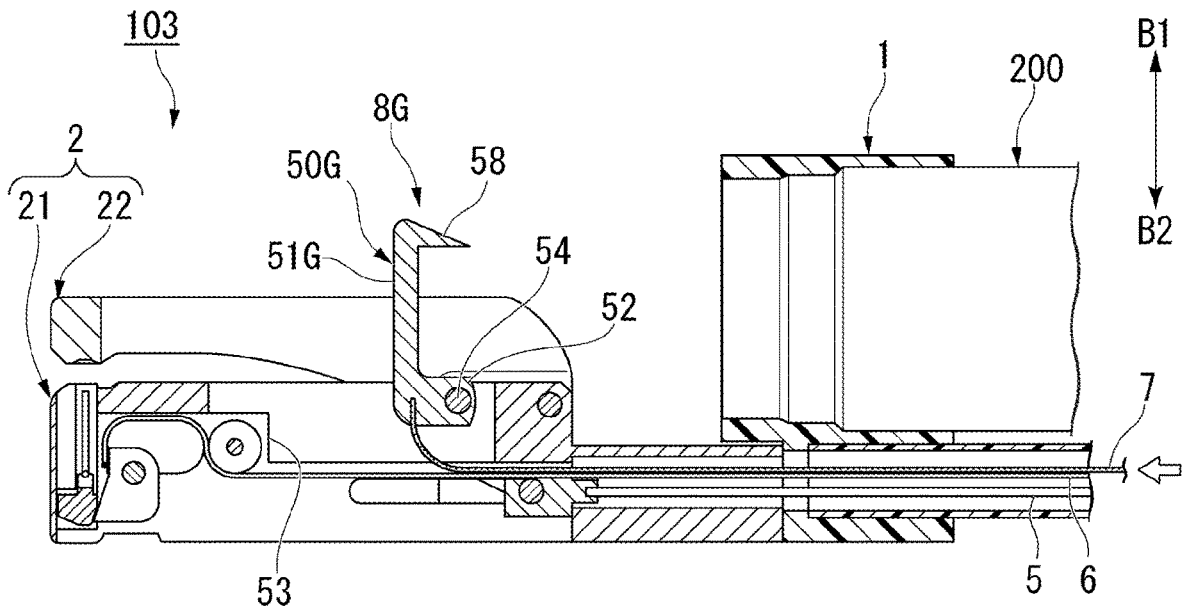
FIG. 31 is a cross-sectional view showing a structure of the medical stapler of the third embodiment.
Figure 32:
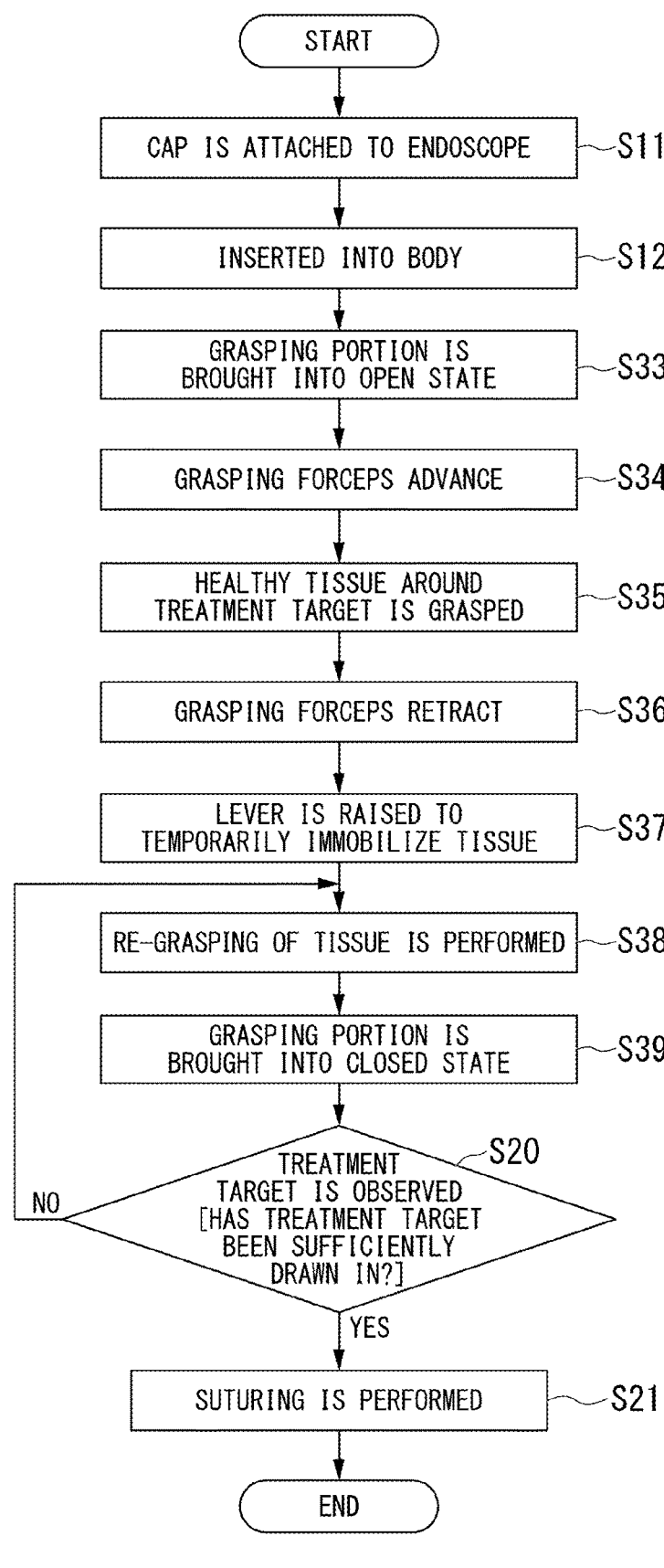
FIG. 32 is a flowchart showing a manipulation procedure using the medical stapler of the third embodiment.

FIGS. 30 and 31 are cross-sectional views showing a structure of the medical stapler 103 of the third embodiment. FIG. 32 is a flowchart showing a manipulation procedure using the medical stapler 103 of the third embodiment. FIGS. 33A to 33D are views showing an operation of the medical stapler 103 of the third embodiment.

As shown in FIGS. 33A to 33D, the medical stapler 103 of the present embodiment is capable of temporarily immobilizing (temporarily fixing) a tissue V on a stapling head 21 so that the tissue V containing a treatment target T drawn into a visual space 25 by grasping forceps G does not return.

A lever portion 8G of the medical stapler 103 shown in FIGS. 30 and 31 is rotatable independently of an open-close operation of an anvil 22. The lever portion 8G includes a temporarily immobilizing portion 58 that can protrude to an upward side B1 from the stapling head 21. The temporarily immobilizing portion 58 is provided on a lever 50G. A shape of the lever 50G in a plan view is not particularly limited. The entire lever portion 8G can be accommodated in a lever accommodating groove 53 formed in the stapling head 21.

As shown in FIG. 30, when the lever 50G is in a state of being accommodated in the lever accommodating groove 53, the temporarily immobilizing portion 58 protrudes outward (to the upward side B1) from an upper surface of a distal-end side of a main body portion 51G of the lever 50G. The temporarily immobilizing portion 58 protrudes from a position on the upper surface of the lever 50G at which it can face the tissue V toward a direction in which the lever 50G rises. The temporarily immobilizing portion 58 has a needle-like or conical shape having a diameter decreasing from a base (proximal end) thereof toward the distal end and having a sharpened distal end.

As shown in FIG. 30, the lever 50G has an angulated U shape in a cross-sectional view, and when the lever 50G is in a state of being accommodated in the lever accommodating groove 53, the main body portion 51G is disposed at a bottom part of the lever accommodating groove 53 and both the temporarily immobilizing portion 58 and a support portion 52 extend to the upward side B1.

In the present embodiment, a lever rotation shaft 54 is disposed at one end side of the support portion 52 on a side opposite to the main body portion 51G. A distal-end side of a lever operation wire 7 is connected to a boundary portion between the main body portion 51G and the support portion 52 of the lever 50G. When the lever operation wire 7 advances, a distal end of the lever 50G rotates rearward with the lever rotation shaft 54 as a center, and the lever 50G gradually protrudes from the stapling head 21 starting from the temporarily immobilizing portion 58. In this way, the lever 50G is raised as shown in FIG. 31.

[Operation of Medical Stapler 103]

Hereinafter, an operation of the medical stapler 102 of the second embodiment will be described along the flowchart of FIG. 32 while referring to FIGS. 30 and 31. Operations the same as those of the medical stapler 100 of the first embodiment will be denoted by the same reference signs, and duplicate description thereof will be omitted.

Figure 33A:
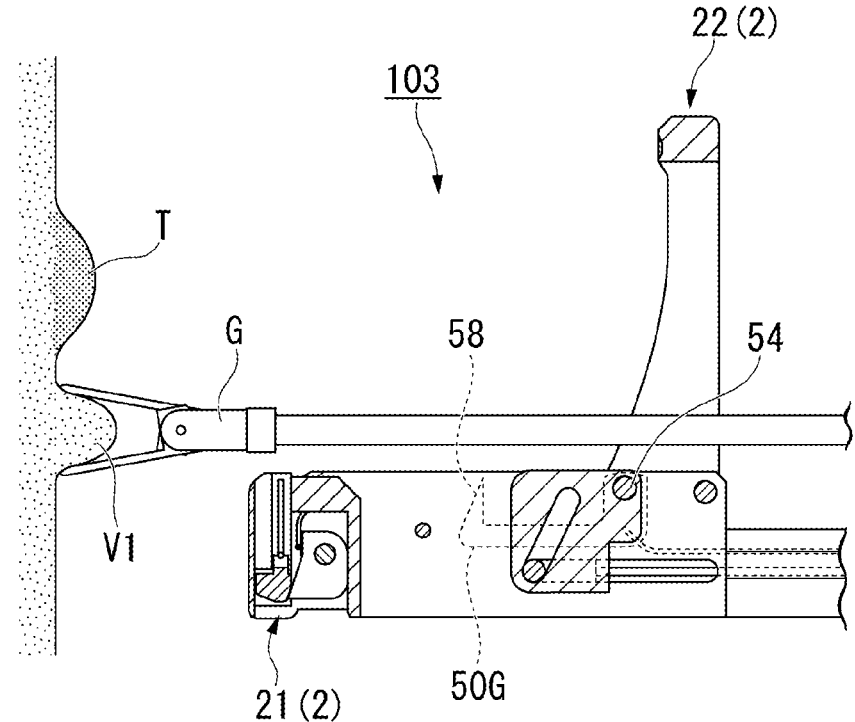
FIG. 33A is a view showing an operation of the medical stapler of the third embodiment.

When the medical stapler 103 of the present embodiment is used, for example, the operator brings a grasping portion 2 into an open state as shown in FIG. 33A (first open-close step S33), advances the grasping forceps G (advancing step S34), and grasps a healthy tissue V1 near the treatment target T using the grasping forceps G (grasping step S35).

Figure 33B:
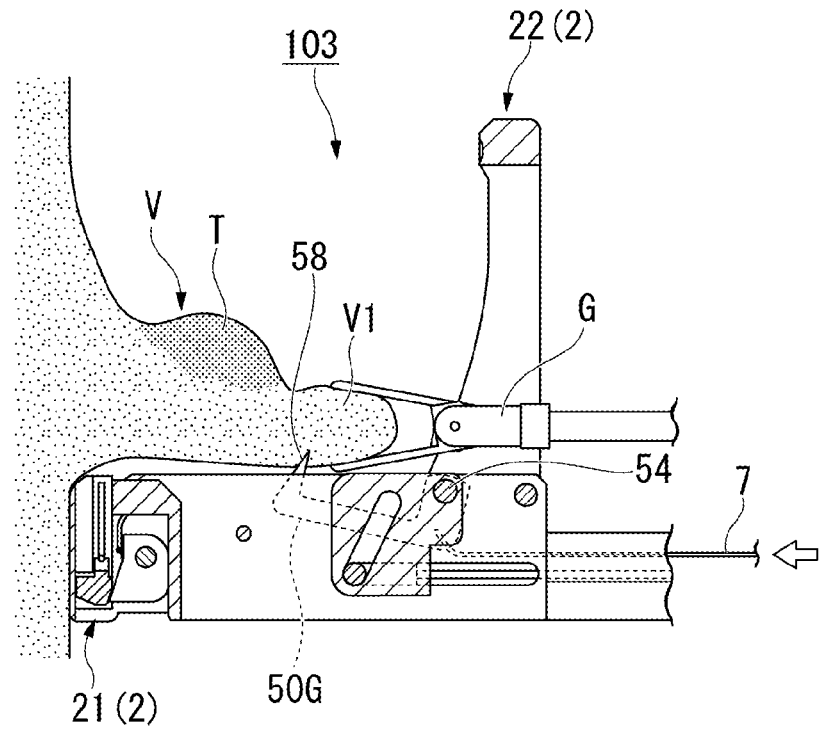
FIG. 33B is a view showing an operation of the medical stapler of the third embodiment.

Next, as shown in FIG. 33B, the operator retracts the grasping forceps G while grasping the tissue V1 around the treatment target T with the grasping forceps G (retracting step S36), and draws in the tissue V (the healthy tissue V1) containing the treatment target T toward the rear of the stapling head 21.

Next, the operator advances the lever operation wire 7 to raise the lever 50G while keeping the grasping portion 2 in an open state (lever raising step S37). In this way, when the temporarily immobilizing portion 58 pierces the tissue V on the stapling head 21, a position of the drawn-in tissue V is fixed and temporarily immobilized.

Figure 33C:
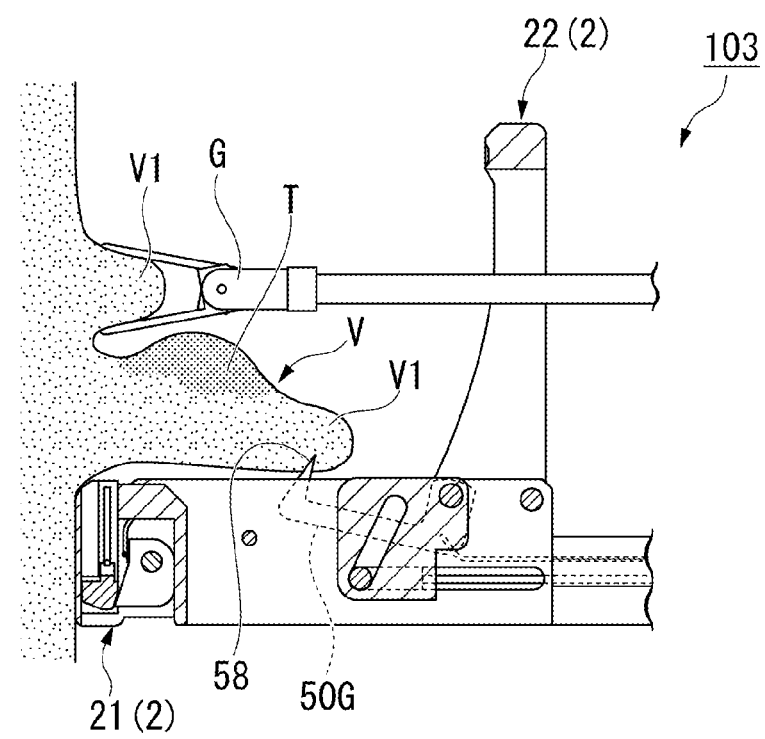
FIG. 33C is a view showing an operation of the medical stapler of the third embodiment.
Figure 33D:
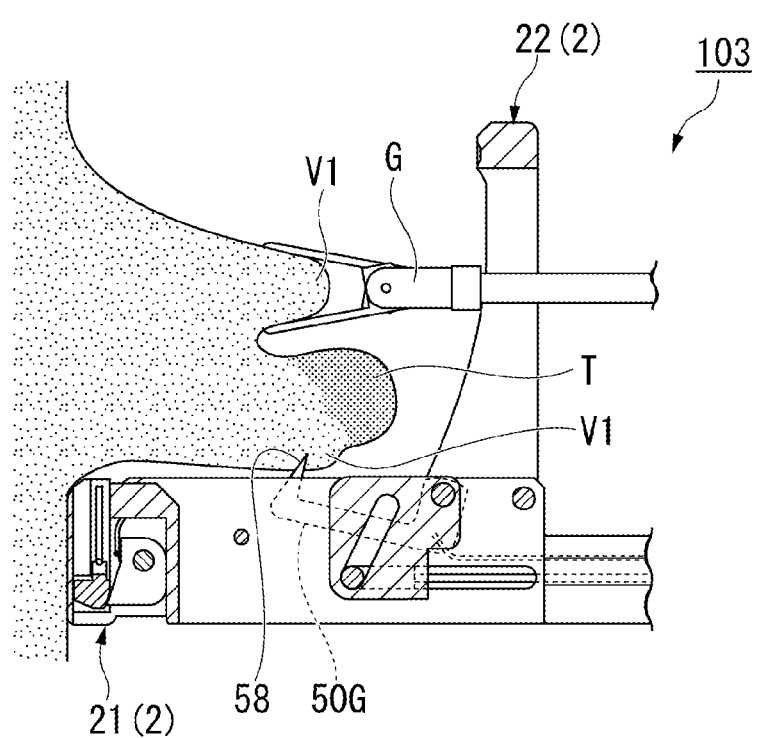
FIG. 33D is a view showing an operation of the medical stapler of the third embodiment.

Next, the operator temporarily releases the grasp on the tissue V due to the grasping forceps G while the tissue V is temporarily immobilized on the stapling head 21 by the temporarily immobilizing portion 58. Thereafter, the grasping forceps G advance again as shown in FIG. 33C to grasp a portion of the tissue V1 around the treatment target T that is different from the portion that has been temporarily immobilized (re-grasping step S38). In this state, when the grasping forceps G retract to the rear again, another portion of the healthy tissue V1 around the treatment target T is further drawn in to the rear of the stapling head 21. In this way, substantially the entire of the treatment target T can be drawn in as shown in FIG. 33D. Thereafter, when the anvil 22 is brought into a closed state (second open-close step S39) and it is possible to ascertain that substantially the entire of the treatment target T has been drawn in, a suturing treatment is performed.

According to the configuration of the present embodiment, since a position of the tissue V1 around the treatment target T grasped by the grasping forceps G can be temporarily immobilized on the stapling head 21, even if the grasp on the tissue V due to the grasping forceps G is temporarily released, the tissue V is prevented from being returned. Therefore, it is easier to grasp the position of the tissue V1 around the treatment target T to be further drawn in, and furthermore it is easier to grasp the portion.

Also, according to the configuration of the present embodiment, even if the treatment target T is large, since the tissue V can be grasped again, the entire treatment target T can be more reliably drawn into the inside of the grasping portion 2. Therefore, it is possible to suture the tissue V1 around the treatment target T while the entire treatment target T is contained therein.

Modified Example 1

In the third embodiment described above, it has been configured such that the tissue V is temporarily immobilized by the temporarily immobilizing portion 58 provided on the lever 50E and having a needle-like or conical shape with a sharpened distal end, but a configuration of temporarily immobilizing the tissue V is not limited thereto.

Figure 34:
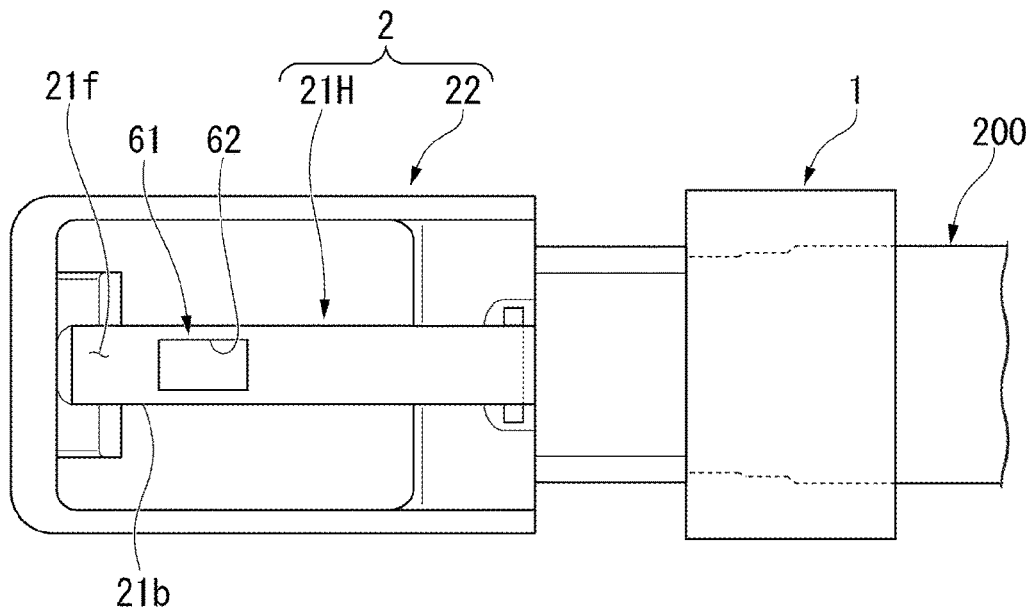
FIG. 34 is a top view showing a configuration of a stapling head of modified example 1 in the third embodiment.
Figure 35:
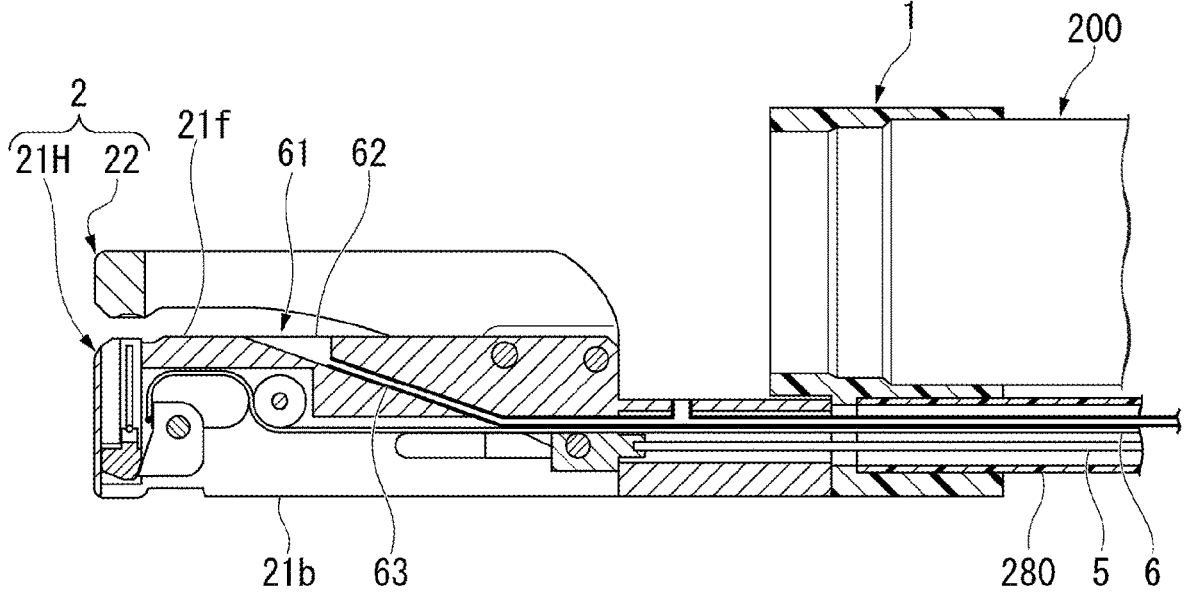
FIG. 35 is a cross-sectional view showing a configuration of the stapling head of modified example 1 in the third embodiment.

FIG. 34 is a top view showing a configuration of a stapling head 21H of modified example 1 in the third embodiment. FIG. 35 is a cross-sectional view showing a configuration of the stapling head 21H of modified example 1 in the third embodiment.

As shown in FIGS. 34 and 35, a suction portion (temporarily immobilizing portion) 61 that can suction the tissue V is provided in the stapling head 21H of modified example 1. The suction portion 61 includes a suction port 62 that opens on an upper surface 21*f* of a first main body portion 21*b* of the stapling head 21, and a suction sheath 63 having one end side connected to the suction port 62.

The suction port 62 has, for example, a rectangular shape in a plan view as shown in FIG. 34, but a shape thereof is not limited thereto. The other end side of the suction sheath 63 is connected to, for example, a suction mechanism which is not shown in the drawings. The suction sheath 63 is a tube with a hollow inside, and is inserted into a wire sheath 280 together with an open-close operation wire 5 and an ejection operation wire 6.

In the present modified example, when the suction mechanism is operated after the tissue V grasped by the grasping forceps G is drawn onto the stapling head 21, a part of the tissue V covering the suction port 62 can be suctioned into the suction port 62. When the suction state of the tissue V is maintained, it is possible to temporarily immobilize the tissue V on the stapling head 21H.

According to such a configuration, since there is minimal invasion to the tissue V, a patient's pain can be alleviated and damage to the tissue can be minimized. Also, since the number of parts can be reduced, a configuration of the grasping portion 2 can be simplified, and costs can be reduced.

While the third embodiment of the present disclosure has been described in detail as above with reference to the drawings, the specific configurations are not limited to the embodiment and may include design changes or the like within a range not departing from the gist of the present invention. Also, it is possible to configure the third embodiment by appropriately combining the components shown in the above-described first embodiment and second embodiment, and the components shown in the modified examples of each of the embodiments.

For example, in each of the embodiments described above, the grasping forceps G have been used as the treatment tool, but the present disclosure is not limited thereto. Instead of the grasping forceps G, a threaded clip or the like may be employed.

Although the respective embodiments and modifications of the present disclosure have been described above, the technical scope of the present disclosure is not limited to the above-described embodiments, and configurations in the respective embodiments and modifications within the scope not departing from the spirit of the present disclosure. It is possible to change the combination of elements, make various changes to each configuration element, or delete each configuration element. For example, the configuration according to any one of above-described embodiments and modifications of the present disclosure may be appropriately combined with each modification of the operation section. The present disclosure is not limited by the above description, but only by the appended claims.

What is claimed is:

1. A medical stapler comprising:
a stapling head including a staple ejection portion;
an anvil openably and closably coupled to the stapling head by a rotation shaft;
a staple receiving portion provided in the anvil, the staple receiving portion being provided at a position facing the staple ejection portion when the stapling head and the anvil are in a closed state;
a lever rotatably provided on the stapling head; and
a lever operation wire connected to the lever and provided to extend in a direction of a proximal end of the stapling head, wherein the lever is capable of raising upward with respect to the stapling head in accordance with advance and retraction of the lever operation wire, and wherein the lever is configured to pass through the anvil when the stapling head and the anvil are in the closed state.

2. The medical stapler according to claim 1, further comprising:
an attachment member detachably attached to a distal-end portion of an endoscope, the attachment member having an opening through which an objective lens of the endoscope is exposed.

3. The medical stapler according to claim 1, wherein the anvil has a first visual space passing through in an open-close direction, and wherein the lever defines and forms a second visual space communicating with the first visual space and through which a treatment tool having grasped a treatment target is able to pass.

4. The medical stapler according to claim 1, wherein the lever includes a temporarily immobilizing portion capable of temporarily immobilizing a treatment target with respect to the stapling head.

5. The medical stapler according to claim 4, wherein the temporarily immobilizing portion protrudes in a direction in which the lever rises.

6. The medical stapler according to claim 4, wherein the temporarily immobilizing portion has a shape which is able to come into contact with a tissue containing the treatment target and which has a diameter decreasing from a proximal end toward a distal end.

7. A medical stapler comprising:
a stapling head including a staple ejection portion;
an anvil openably and closably coupled to the stapling head by a rotation shaft;
a staple receiving portion provided in the anvil, the staple receiving portion being provided at a position facing the staple ejection portion when the stapling head and the anvil are in a closed state;
a lever rotatably provided on the stapling head, wherein the lever is configured to pass through the anvil when the stapling head and the anvil are in a closed state; and
a temporarily immobilizing portion provided in the stapling head, the temporarily immobilizing portion being capable of temporarily immobilizing a treatment target with respect to the stapling head.

8. The medical stapler according to claim 7, wherein the temporarily immobilizing portion includes:
a suction port which is able to face a tissue containing the treatment target and opens on an upper surface of the stapling head; and
a suction sheath having one end side connected to the suction port and is able to communicate with the suction port.

9. A suturing method comprising:

an insertion step of inserting a medical stapler and an endoscope into a body;

an advancing step of causing a treatment tool to protrude from the endoscope and advancing the treatment tool with respect to the medical stapler;

a first open-close step of bringing an anvil into an open state with respect to a stapling head at a portion close to a treatment target;

a grasping step of grasping a tissue containing the treatment target inside the body with the treatment tool;

a retracting step of retracting the treatment tool relative to the medical stapler to draw in the treatment target to a proximal-end side of the medical stapler with respect to a staple ejection position;

a second open-close step of bringing the anvil into a closed state with respect to the stapling head to fix the tissue;

a lever raising step of raising a lever upward with respect to the stapling head, wherein the lever is configured to pass through the anvil when the anvil and the stapling head are in the closed state;

an observation step of projecting the treatment target within a field of view showing the endoscope; and a suturing step of ejecting a staple from the stapling head of the medical stapler to suture a circumference of the treatment target.

10. The suturing method according to claim 9, wherein the lever raising step is configured to raise the lever by advancing and retracting a lever operation wire, and turn up the tissue by raising the lever.

11. The suturing method according to claim 10, wherein the lever raising step is performed after the second open-close step.

12. A suturing method comprising:

an insertion step of inserting a medical stapler and an endoscope into a body;

an advancing step of causing a treatment tool to protrude from the endoscope and advancing the treatment tool with respect to the medical stapler;

a first open-close step of bringing an anvil into an open state with respect to a stapling head at a portion close to a treatment target;

a lever raising step of raising a lever upward with respect to the stapling head;

a grasping step of grasping a tissue containing the treatment target inside the body with the treatment tool;

a retracting step of retracting the treatment tool relative to the medical stapler to draw in the treatment target to a proximal-end side of the medical stapler with respect to a staple ejection position;

a second open-close step of bringing the anvil into a closed state with respect to the stapling head;

a pressing step of pressing the treatment target drawn in to an endoscope side from above by lowering the lever;

an observation step of projecting the treatment target within a field of view showing the endoscope; and a suturing step of ejecting a staple from the stapling head of the medical stapler to suture a circumference of the treatment target.

13. The suturing method according to claim 12, wherein the advancing step is configured to advance the treatment tool through a first visual space of the anvil and a second visual space of the lever which communicate with each other, and wherein the retracting step is configured to retract the treatment tool through the first visual space and the second visual space.

14. The suturing method according to claim 12, further comprising a re-grasping step of re-grasping a tissue containing the treatment target with the treatment tool after temporarily immobilizing the treatment target in the lever raising step.

* * * * *